United States Patent
Szafran et al.

(10) Patent No.: US 12,295,555 B2
(45) Date of Patent: May 13, 2025

(54) BIOPSY TOOL AND METHOD FOR REMOVING A TISSUE SAMPLE

(71) Applicant: Szafran Biopsy AB, Lidingö (SE)

(72) Inventors: Rebecca Szafran, Lidingö (SE); David Skantze, Saltsjö-boo (SE); Magnus Olsen, Vallentuna (SE)

(73) Assignee: Szafran Biopsy AB, Lidingö (SE)

( * ) Notice: Subject to any disclaimer, the term of this patent is extended or adjusted under 35 U.S.C. 154(b) by 773 days.

(21) Appl. No.: 17/612,346

(22) PCT Filed: May 27, 2020

(86) PCT No.: PCT/SE2020/050539
§ 371 (c)(1),
(2) Date: Nov. 18, 2021

(87) PCT Pub. No.: WO2020/242371
PCT Pub. Date: Dec. 3, 2020

(65) Prior Publication Data
US 2022/0240905 A1    Aug. 4, 2022

(30) Foreign Application Priority Data
May 29, 2019  (SE) .................................... 1950644-3

(51) Int. Cl.
*A61B 10/02*  (2006.01)
*A61B 17/00*  (2006.01)
*A61B 17/3205*  (2006.01)

(52) U.S. Cl.
CPC .... *A61B 10/0266* (2013.01); *A61B 17/32053* (2013.01); *A61B 2010/0208* (2013.01); *A61B 2017/00477* (2013.01)

(58) Field of Classification Search
CPC ............ A61B 10/02; A61B 2010/0208; A61B 10/0233; A61B 10/0266; A61B 10/0275;
(Continued)

(56) References Cited

U.S. PATENT DOCUMENTS

| | | | |
|---|---|---|---|
| 4,461,305 A | 7/1984 | Cibley | |
| 5,573,008 A * | 11/1996 | Robinson | A61B 10/0266 600/567 |

(Continued)

FOREIGN PATENT DOCUMENTS

| | | |
|---|---|---|
| CN | 105228532 A | 1/2016 |
| CN | 106999172 A | 8/2017 |

(Continued)

OTHER PUBLICATIONS

Machine translation of EP 1293167 (Year: 2024).*

*Primary Examiner* — Puya Agahi
*Assistant Examiner* — Alice Ling Zou
(74) *Attorney, Agent, or Firm* — Capitol City TechLaw

(57) ABSTRACT

The invention relates to a biopsy tool (10) for removing a tissue sample. The biopsy tool (10) is configured to be altered between an incision state and a severing state. The biopsy tool (10) comprises: an elongated outer tubular member (20) wherein a distal end (22) of the outer tubular member (20) comprises a cutting edge (24); an elongated inner tubular member (30) arranged inside the outer tubular member (20); and a cutting wire (40). The outer and inner tubular members (20, 30) are rotatable in relation to each other around a rotational axis (R). The outer tubular member (20) comprises a first aperture (25) and the inner tubular member (30) comprises a second aperture (35). The cutting wire (40) is spring biased and configured to be arranged in association with the first aperture (25) of the outer tubular member (20). The biopsy tool (10) is configured to obtain the severing state by rotational movement of the outer tubular member (20) and/or the inner tubular member (30), so that the first aperture (25) and the second aperture (35) overlap, whereby the cutting wire (40) is displaced perpendicularly to the rotational axis (R). The invention also relates
(Continued)

to a method for removing a tissue sample by using a biopsy tool (10).

25 Claims, 13 Drawing Sheets

(58) Field of Classification Search
CPC ......... A61B 2017/32002; A61B 2017/320032; A61B 2017/32004; A61B 2017/32006–320064; A61B 17/3205–32053
See application file for complete search history.

(56) References Cited

U.S. PATENT DOCUMENTS

| | | | |
|---|---|---|---|
| 5,913,857 A * | 6/1999 | Ritchart | A61B 18/1482 606/45 |
| 6,238,355 B1 | 5/2001 | Daum | |
| 6,454,727 B1 * | 9/2002 | Burbank | A61B 10/0266 600/567 |
| 2003/0082797 A1 * | 5/2003 | Rastorgoueff | G01N 1/08 435/309.1 |
| 2004/0167427 A1 | 8/2004 | Quick et al. | |
| 2006/0030785 A1 | 2/2006 | Field et al. | |
| 2006/0149162 A1 * | 7/2006 | Daw | A61B 10/0275 600/564 |
| 2007/0142743 A1 * | 6/2007 | Provencher | A61B 10/0266 600/564 |
| 2007/0249960 A1 * | 10/2007 | Williamson | A61B 17/32053 600/564 |
| 2014/0276810 A1 | 9/2014 | Raybin et al. | |
| 2016/0151085 A1 | 6/2016 | McDonald | |
| 2017/0189054 A1 * | 7/2017 | Fujii | A61B 17/32053 |
| 2019/0090861 A1 | 3/2019 | Snow et al. | |

FOREIGN PATENT DOCUMENTS

| | | |
|---|---|---|
| CN | 109788969 A | 5/2019 |
| EP | 1293167 A3 | 3/2003 |
| GB | 1063653 | 3/1967 |
| JP | 2000152941 A | 6/2000 |
| JP | 2007-54449 A | 3/2007 |
| JP | 2014-200299 A | 10/2014 |
| WO | 2004075759 A1 | 9/2004 |

* cited by examiner

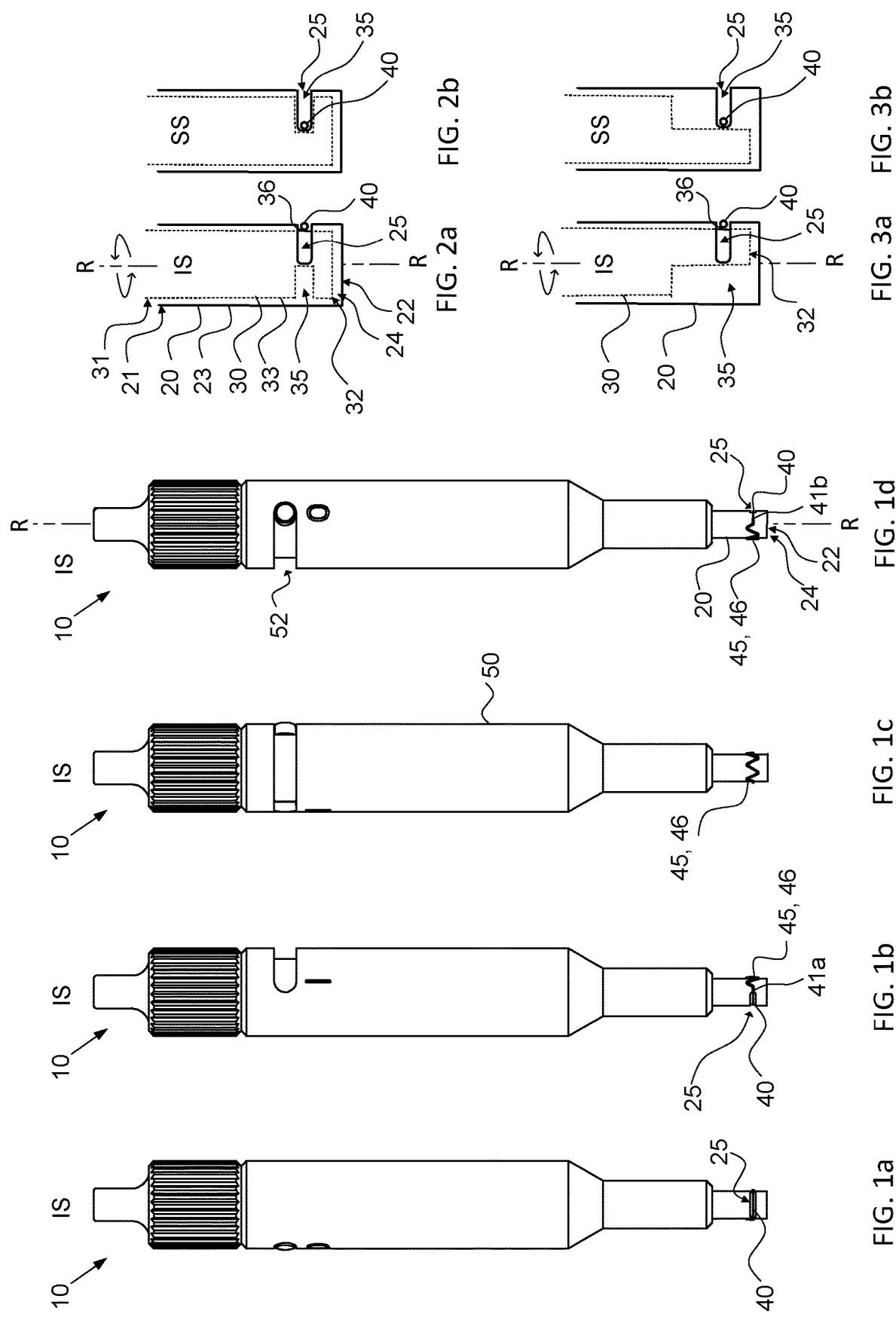

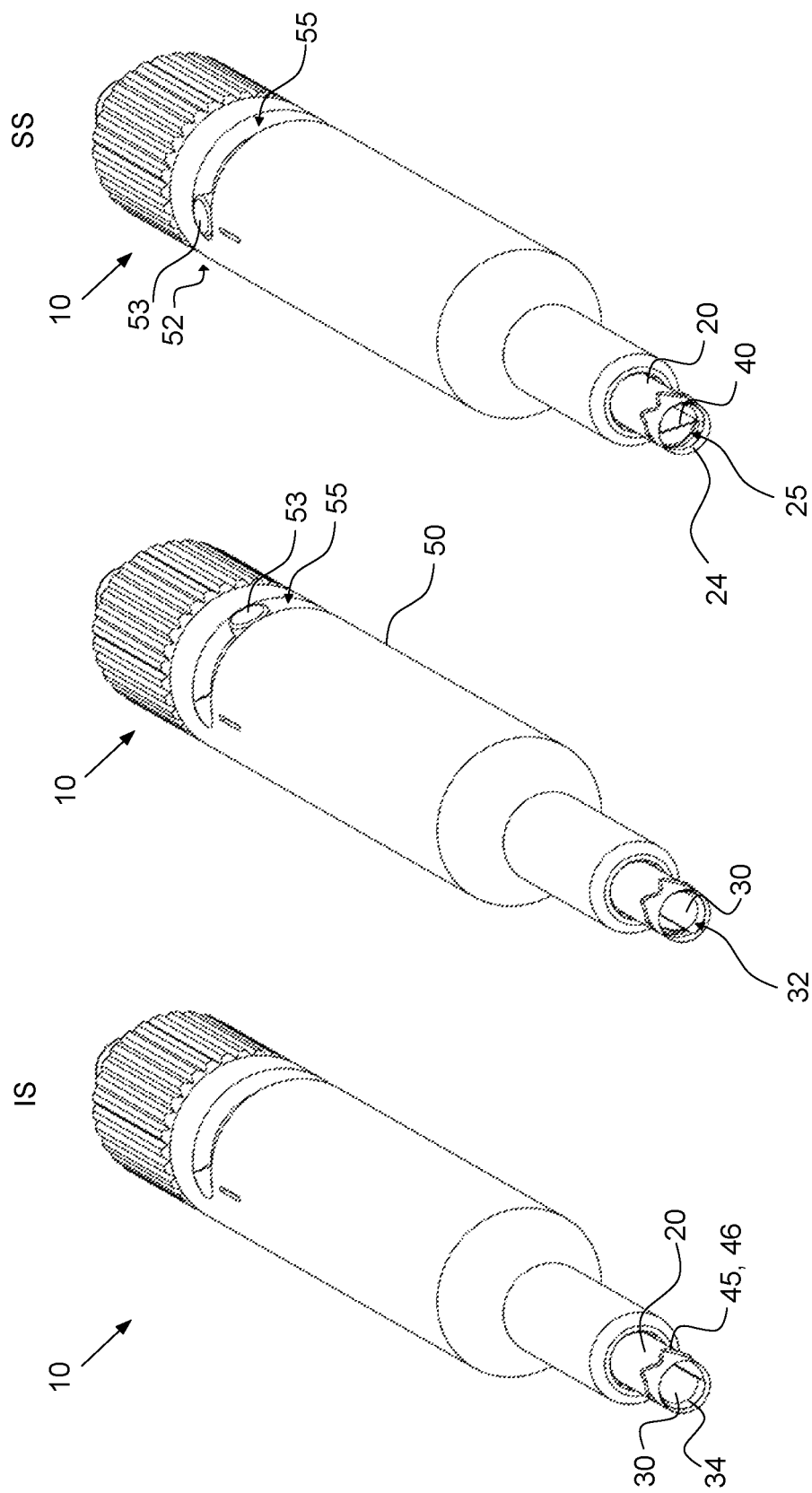

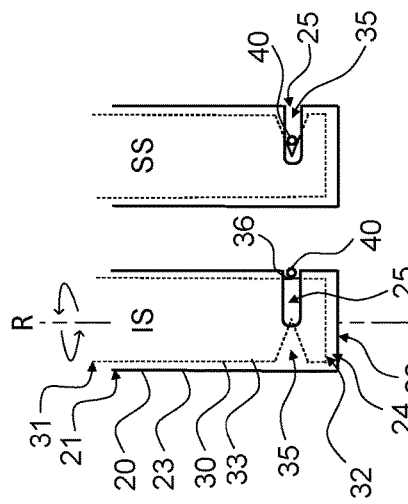
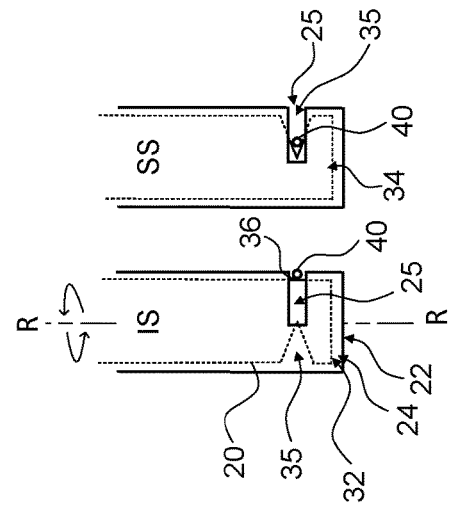
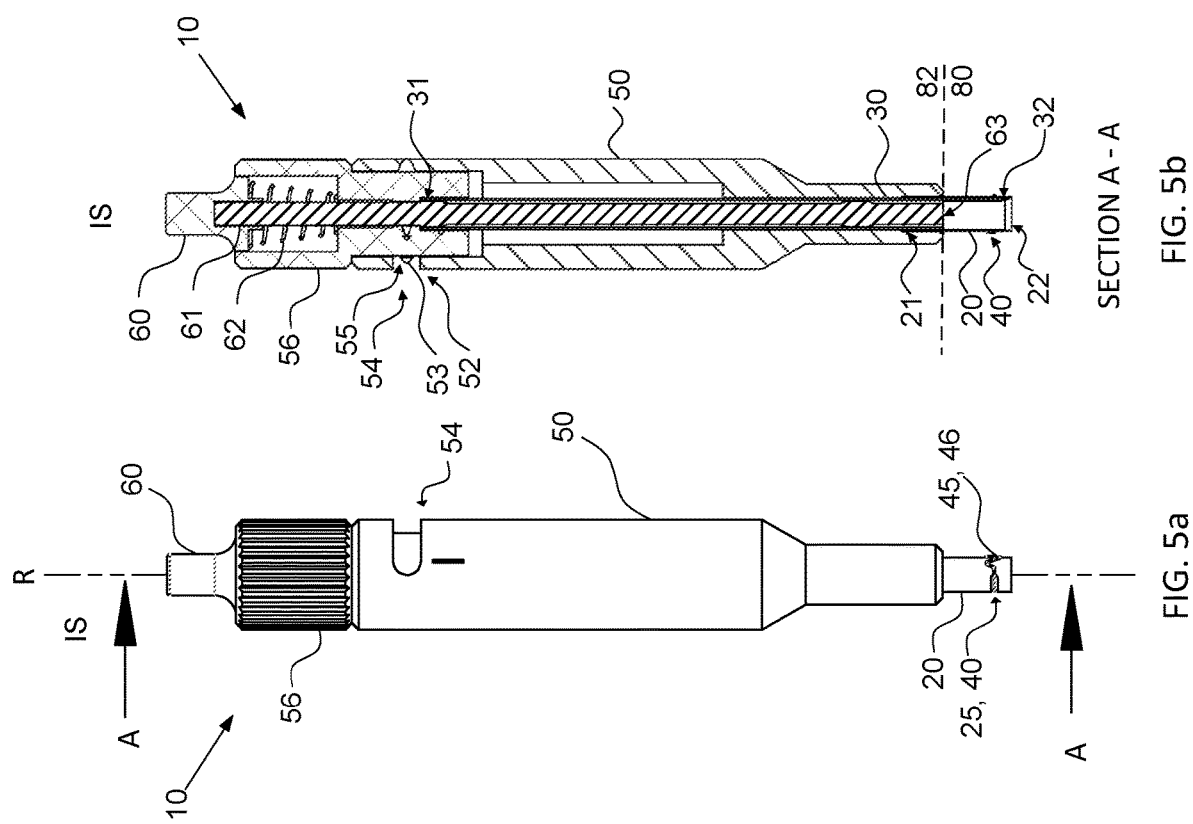

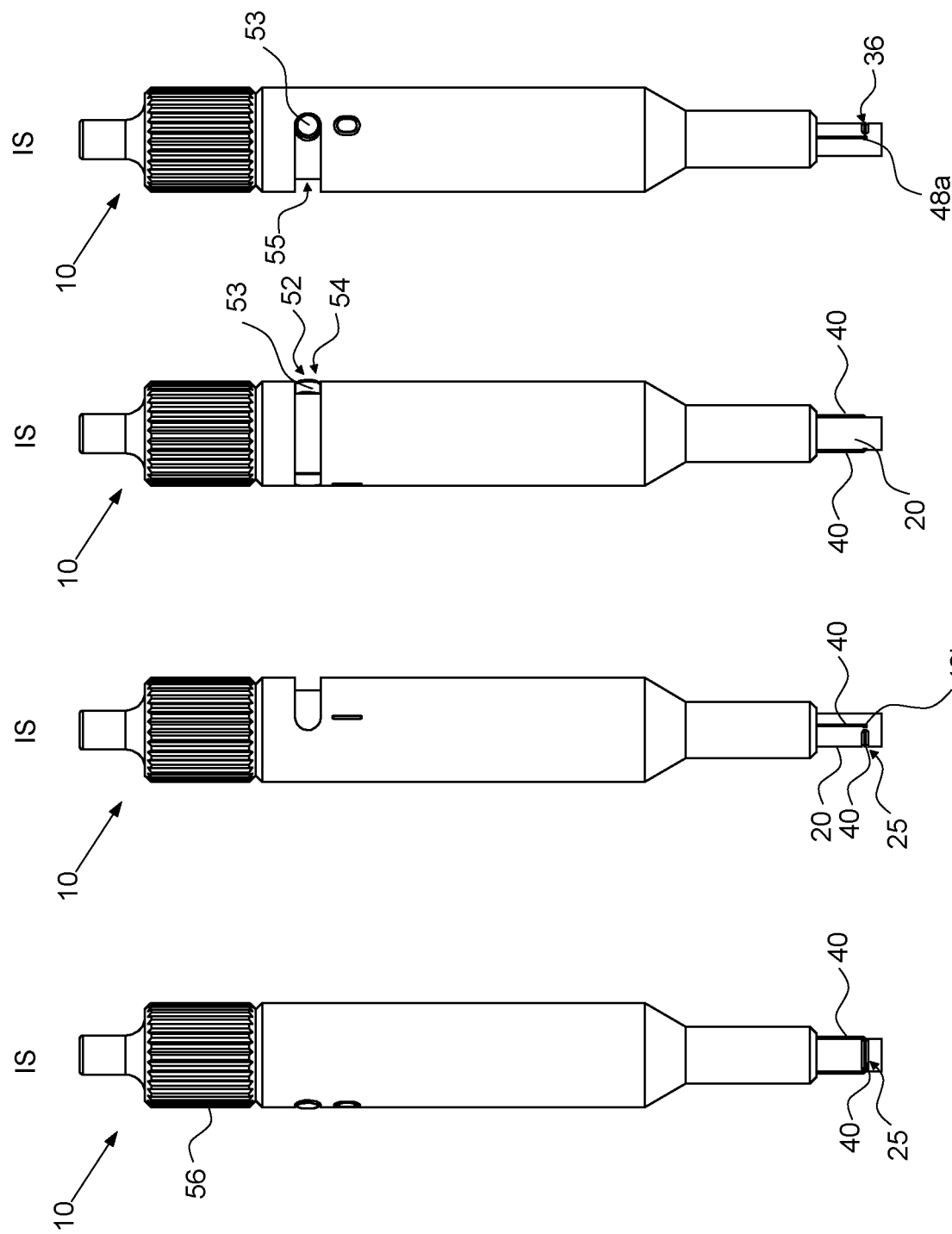

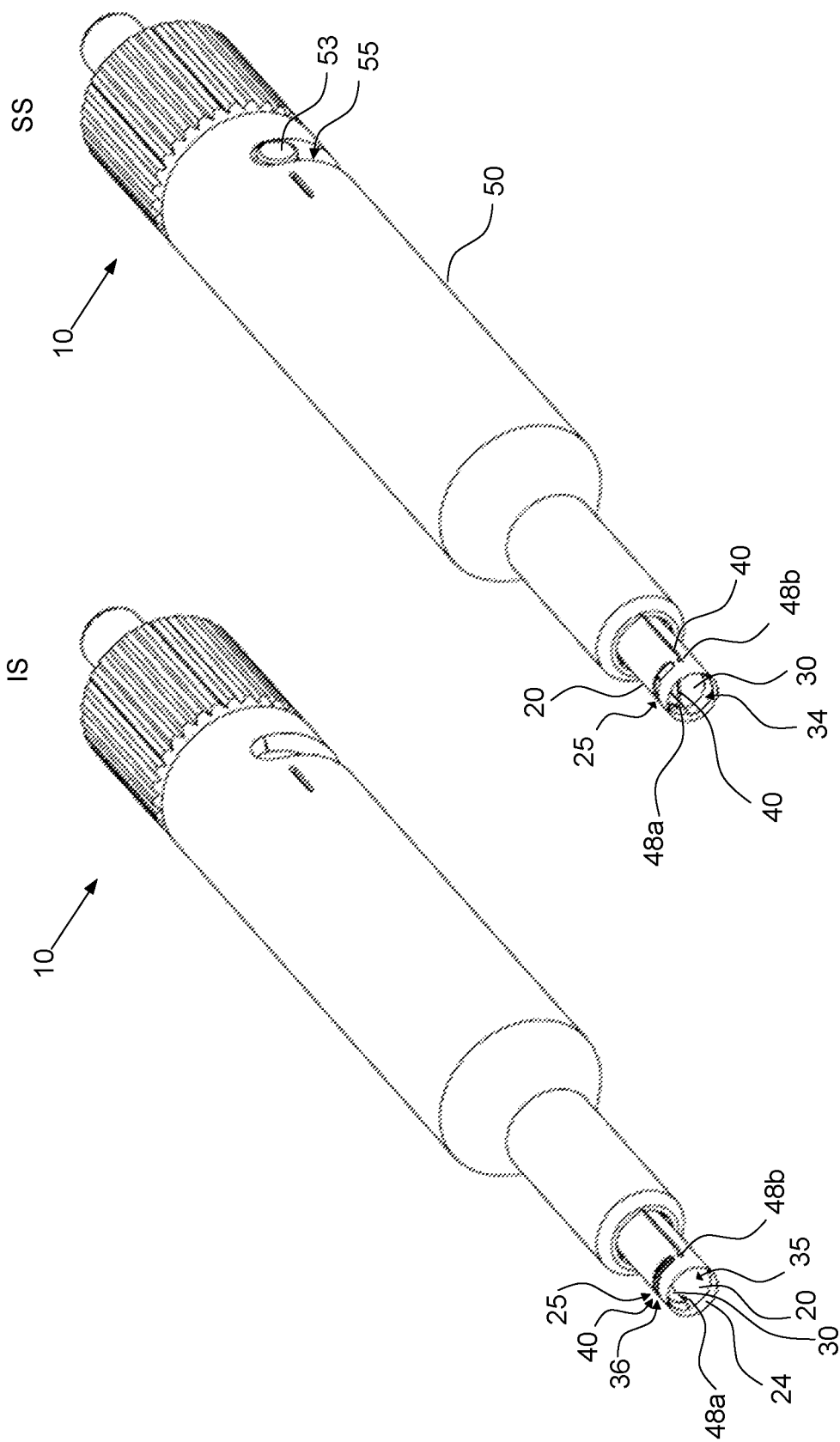

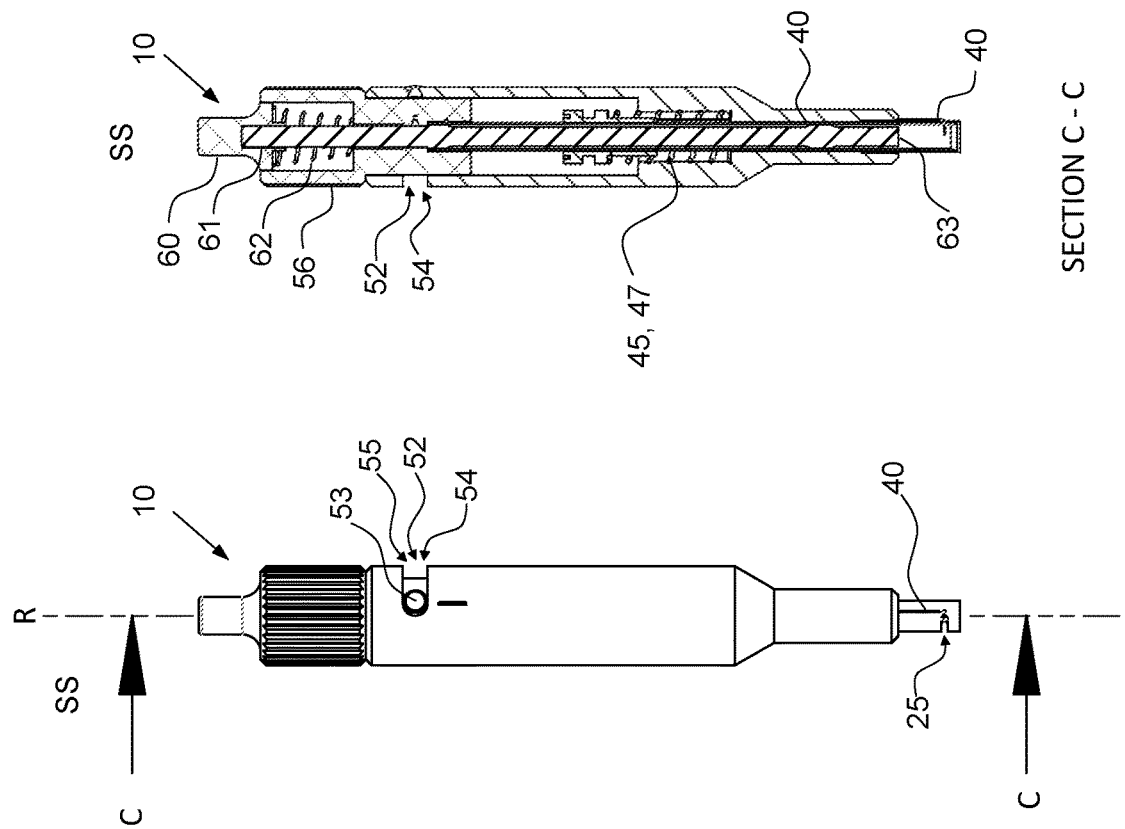
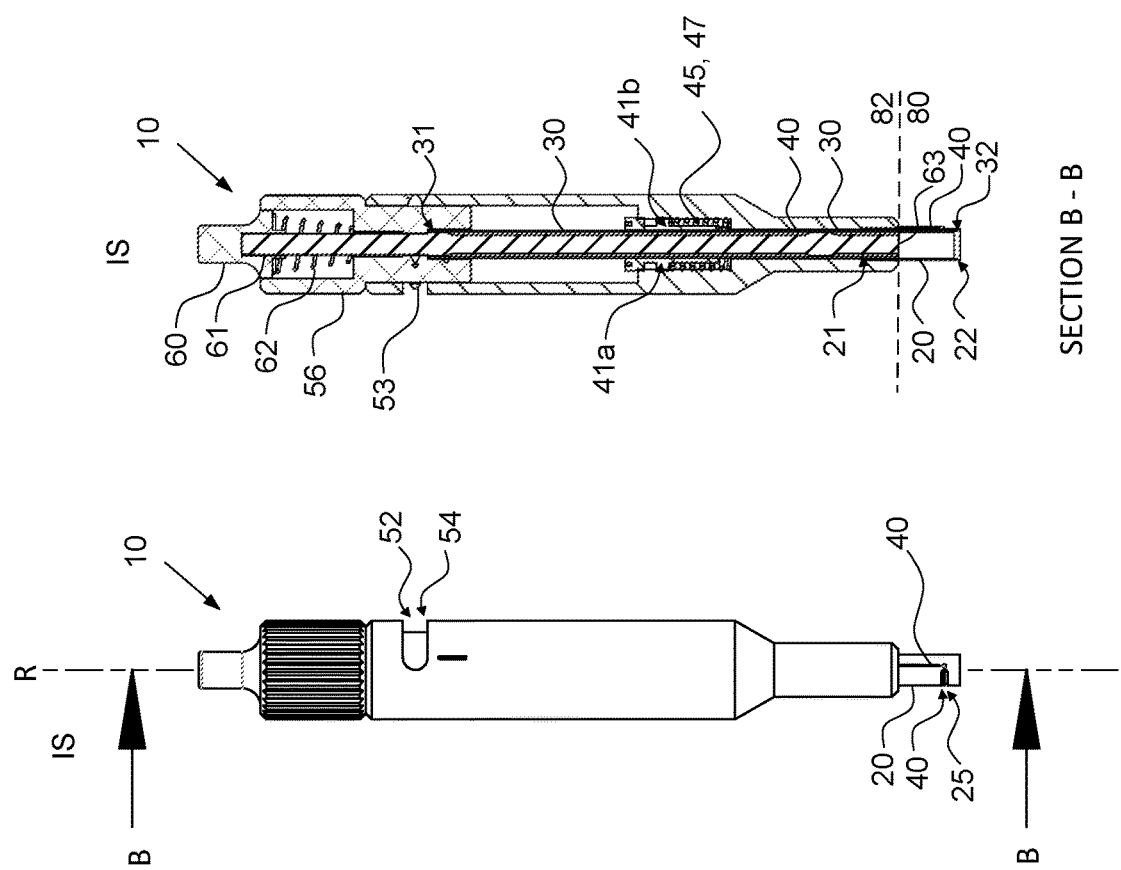

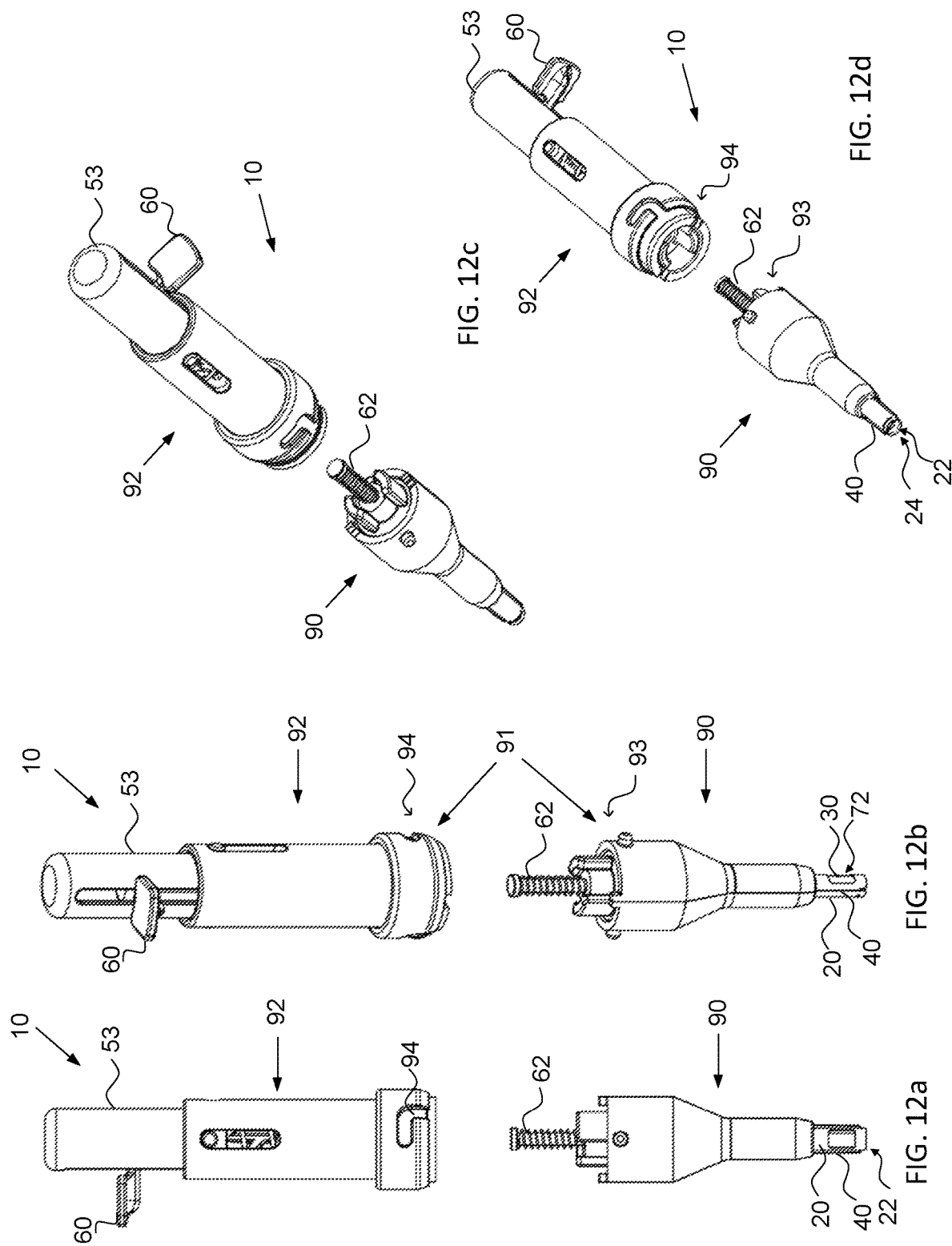

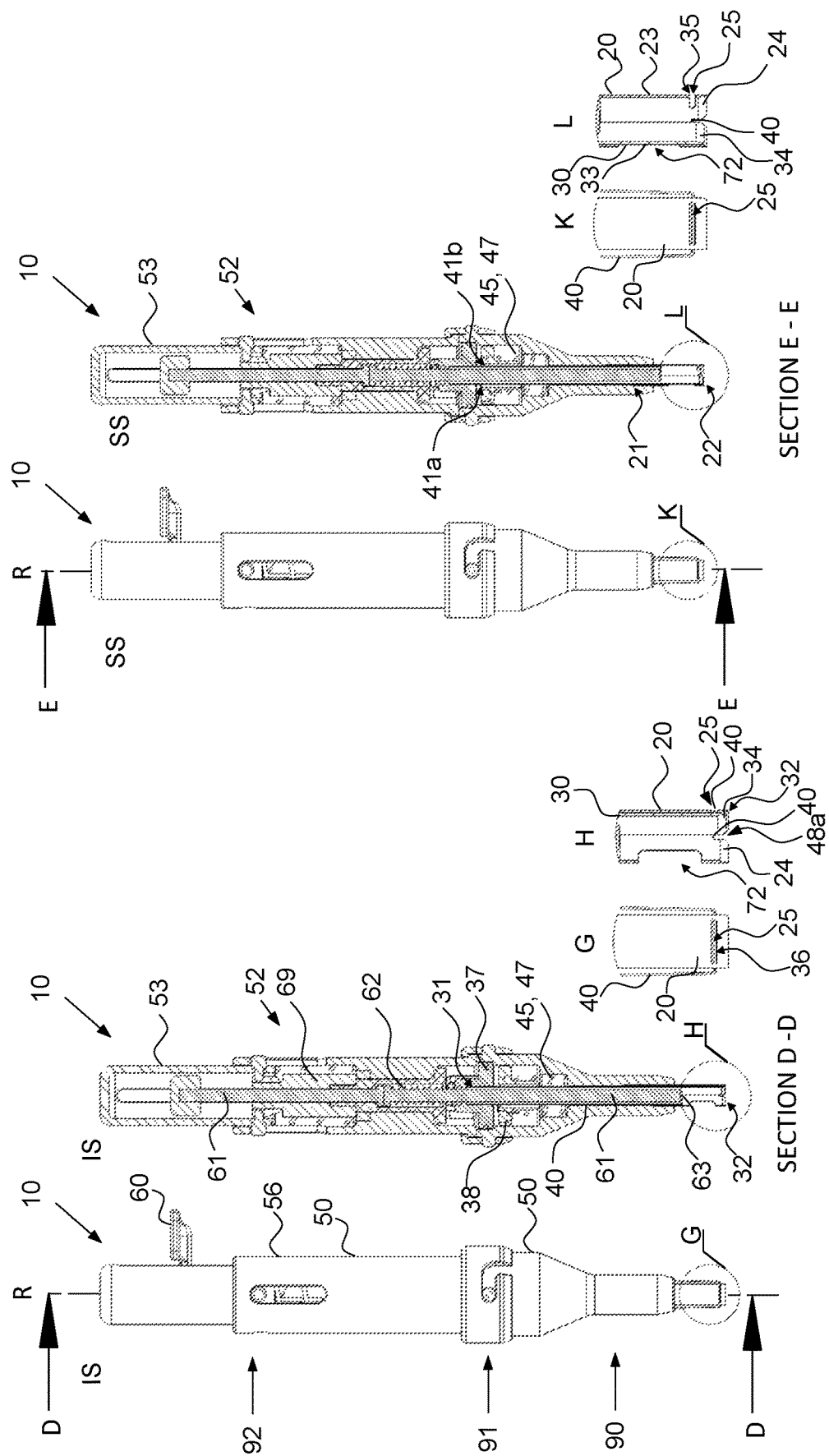

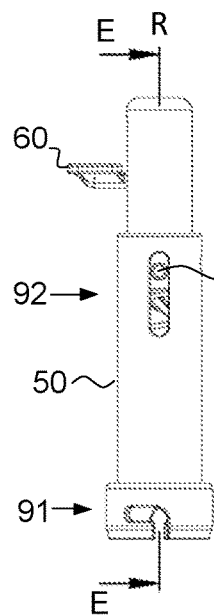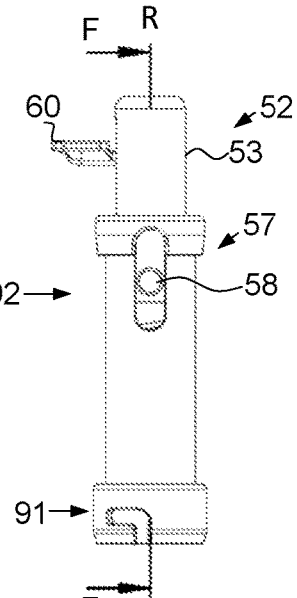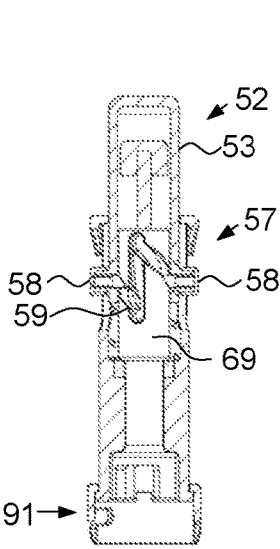
FIG. 14a  　　SECTION E-E  　FIG. 14c  　SECTION F-F
　　　　　　　FIG. 14b　　　　　　　　　　　FIG. 14d
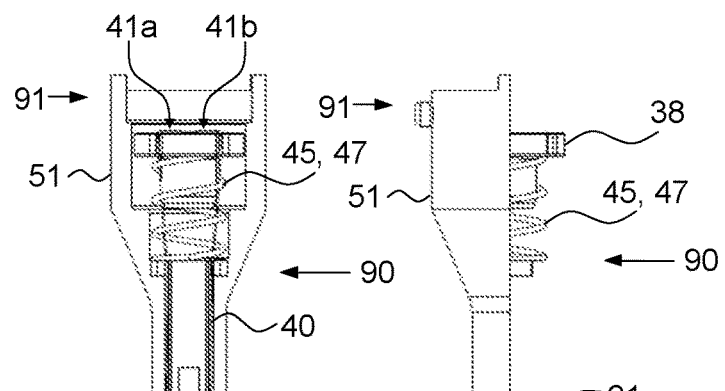
FIG. 14e　　　　　　　　　FIG. 14f
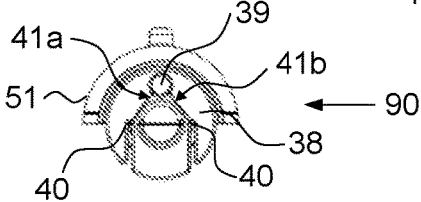
FIG. 14g

BIOPSY TOOL AND METHOD FOR REMOVING A TISSUE SAMPLE

This application claims priority under 35 USC 119 (a)-(d) to SE patent application No. 1950644-3, which was filed on May 29, 2019, the entire contents of which are incorporated herein by reference.

TECHNICAL FIELD

The present invention relates to a biopsy tool for removing a tissue sample. The invention also relates to a method for removing a tissue sample by using such a biopsy tool.

BACKGROUND

A biopsy involves extraction of a tissue sample for analysis. Biopsies can be performed by various instruments and methods and a tissue sample can be taken from almost anywhere on or in a body, including the skin, organs and other structures. A biopsy removes cells and tissues, which are analysed in order to identify abnormal cells, which can help to diagnose a specific condition. A skin biopsy is often used to diagnose skin conditions, such as inflammatory disease, autoimmune disease, skin cancer and other cancers in the skin. It can also be used for radical excision of small melanoma lesions. Cancer is a leading cause of death worldwide, and the number of cancer diagnoses are constantly increasing. Hence, sampling of tissue is of great importance in order to discover cancer at an early stage. By diagnosing diseases early, the chances of effective treatment and survival increases. If a condition has already been diagnosed, biopsy can also be used to assess its severity (such as the degree of inflammation) and grade (such as the aggressiveness of a cancer). This information can be very useful when deciding on the most appropriate treatment, and assessing how well a person responds to a particular type of treatment. It can also be useful in helping to determine a person's overall prognosis. Biopsy sampling is thus becoming more and more important. However, the availability of biopsy sampling may often be limited, since tissue sampling and analysis is very expensive. The sampling procedure consumes a lot of time and resources in the form of medical equipment and health care professionals. The tissue sampling procedures are also technically demanding since the pain and discomfort for the patient has to be kept down, while simultaneously obtaining a representative sample. A representative sample is of great significance in order to reduce the risk of diagnostic errors and enable a reliable analysis.

One known solution for removing a tissue sample is disclosed in document US 2007/0249960 1A. The document discloses a biopsy punch and method for removing a biopsy sample from a biopsy area of a patient.

Another known solution for removing a tissue sample is disclosed in US2016/0151085 A1. The document discloses a biopsy tool comprising an elongated shaft and a cutting wire.

SUMMARY OF THE INVENTION

An object of the present invention is to achieve an advantageous biopsy tool for removing a tissue sample.

Another object of the invention is a time- and cost-efficient removal of a tissue sample.

The herein mentioned objects are achieved by:
a biopsy tool for removing a tissue sample, and a method for removing a tissue sample by using such a biopsy tool, according to the appended independent claims.

Hence, according to an aspect of the present disclosure a biopsy tool for removing a tissue sample is provided. The biopsy tool is configured to be altered between an incision state and a severing state. The biopsy tool comprises an elongated outer tubular member extending longitudinally between a proximal end and a distal end, wherein the outer tubular member comprises a first circumferential wall and wherein the distal end of the outer tubular member comprises a cutting edge; an elongated inner tubular member arranged inside the outer tubular member, wherein the inner tubular member comprises a proximal end, a distal end and a second circumferential wall; and a cutting wire.

The outer and inner tubular members are rotatable in relation to each other around a rotational axis. The outer tubular member comprises a first aperture in the first circumferential wall and the inner tubular member comprises a second aperture in the second circumferential wall, wherein the first and second apertures extend in a direction perpendicular to the rotational axis. The cutting wire is spring biased and is configured to be arranged in association with the first aperture of the outer tubular member. The biopsy tool is configured to obtain the severing state by rotational movement of the outer tubular member and/or the inner tubular member, so that the first aperture and the second aperture overlap, whereby the cutting wire is displaced perpendicularly to the rotational axis.

According to another aspect of the present disclosure, a method for removing a tissue sample by using a biopsy tool as disclosed herein is provided. The biopsy tool being configured to be altered between an incision state and a severing state, the biopsy tool comprising: an elongated outer tubular member extending longitudinally between a proximal end and a distal end, wherein the outer tubular member comprises a first circumferential wall and the distal end of the outer tubular member comprises a cutting edge; an elongated inner tubular member arranged inside the outer tubular member, wherein the inner tubular member comprises a proximal end, a distal end and a second circumferential wall; and a cutting wire, wherein the outer and inner tubular members are rotatable in relation to each other around a rotational axis; wherein the outer tubular member comprises a first aperture in the first circumferential wall and the inner tubular member comprises a second aperture in the second circumferential wall, wherein the first and second apertures extend in a direction perpendicular to the rotational axis, wherein the cutting wire is spring biased and is configured to be arranged in association with the first aperture of the outer tubular member. The method comprises the steps of: incising the tissue by means of the cutting edge of the outer tubular member; rotating the outer tubular member and/or the inner tubular member, so that the first aperture and the second aperture overlap, whereby the severing state is obtained and the cutting wire is displaced perpendicularly to the rotational axis; and rotating at least the outer tubular member and the inner tubular member around the rotational axis.

Today, punch biopsy is the most widely used technique for skin biopsy. During a punch biopsy, a user, usually a medical practitioner such as a doctor, uses a circular tool to cut into the tissue. The doctor must then use forceps and a scissor or a scalpel in order to fully remove the tissue sample from the body. The doctor may also need assistance from other trained health care personnel to e.g. wipe up blood in order to keep the sampling area clean enough to see what and where to cut while the doctor holds the tissue sample with one hand while cutting of the tissue sample with the other hand.

By incising the tissue by means of the cutting edge of the outer tubular member and severing and separating the tissue sample from the tissue sample area by means of the spring biased cutting wire as in the present disclosure, a tissue sample may be removed without the need to utilize other tools such as scalpels, surgical scissors and/or forceps. In addition, by means of the present disclosure, the whole sampling procedure may be conducted by only one person, with only one hand. Tissue samples may thus be collected in a time- and cost-efficient manner.

By means of the present disclosure, a tissue sample can be removed from a body without having to pull in the tissue with forceps and without freehand cutting. As a result, the sampling procedure may be less disturbing and painful for the patient, when the removal of the tissue sample is conducted quickly and with ease. Due to the efficient removal, cleaner cuts are achieved which result in that the actual tissue sample is exposed to less damages and a more representative sample is obtained. A straight cut, essentially perpendicular to the skin, is obtained, which may enable a more adequate analysis of the tissue sample. A representative sample is of great importance in making a reliable assessment when analysing. By means of the present disclosure, the tissue sampling depth may be easier to observe and control during incising. Consequently, the tissue sample area will be left less traumatised and advantageous healing may be achieved. Also, a less uncomfortable patient may also facilitate a more favourable sampling situation, which may result in a higher quality of the tissue sample and a better and safer working situation for the person taking the sample.

According to the present disclosure, the cutting into the tissue, i.e. incising, is achieved by means of the cutting edge at the distal end of the outer tubular member, while the cutting off, i.e. severing, is achieved by means of the spring biased cutting wire. By means of the cutting wire being spring biased, an efficient and semiautomatic chopping off movement is achieved at the base of the tissue sample, where the base of the tissue sample is located at a certain depth into the body tissue. Thereby, an efficient severing of a tissue sample may be achieved e.g. in the layer of fat tissue below the dermis. Due to the easy handling of the biopsy tool, the person using the biopsy tool needs less training and practise to use the tool, which further reduces the expenditure of time and costs relating to tissue sampling. In addition, since the demand for multiple instruments for tissue sampling is reduced, the handling of sharp blood contaminated instruments between healthcare worker may significantly decrease. Thereby, increased safety for healthcare workers during the tissue sampling procedure may be achieved.

Thus, by means of the biopsy tool according to the present disclosure, the actual time for taking a tissue sample, the training time and the number of individuals needed for sampling is reduced, which significantly reduces the cost in respect to both financial and human assets. Other synergy effects are that the pain and discomfort for the patient is reduced while the quality of the tissue samples taken increase. Thus, by the present disclosure, an advantageous biopsy tool and effective sampling procedure is obtained whereby representative tissue samples for analysis is achieved.

Further objects, advantages and novel features of the present invention will become apparent to one skilled in the art from the following details, and also by putting the invention into practice. Whereas the invention is described below, it should be noted that it is not restricted to the specific details described. Specialists having access to the teachings herein will recognise further applications, modifications and incorporations within other fields, which are within the scope of the invention.

BRIEF DESCRIPTION OF THE DRAWINGS

For fuller understanding of the present invention and further objects and advantages of it, the detailed description set out below should be read together with the accompanying drawings, in which the same reference notations denote similar items in the various drawings, and in which:

FIGS. 1a-1d schematically illustrate a biopsy tool according to an example of the present disclosure;

FIGS. 2a-2b, schematically illustrate details of a biopsy tool according to examples of the present disclosure;

FIGS. 3a-3b, schematically illustrate details of a biopsy tool according to examples of the present disclosure;

FIGS. 4a-4c, schematically illustrate a biopsy tool according to an example of the present disclosure;

FIGS. 5a-5b schematically illustrate a biopsy tool according to an example of the present disclosure;

FIGS. 6a-6b schematically illustrate details of a biopsy tool according to examples of the present disclosure;

FIGS. 7a-7b schematically illustrate details of a biopsy tool according to examples of the present disclosure;

FIGS. 8a-8d schematically illustrate a biopsy tool according to an example of the present disclosure;

FIGS. 9a-9b schematically illustrate a biopsy tool according to an example of the present disclosure;

FIGS. 10a-10d schematically illustrate a biopsy tool according to an example of the present disclosure;

FIGS. 12a-12d schematically illustrate a biopsy tool according to an example of the present disclosure;

FIGS. 13a-13h schematically illustrate a biopsy tool according to an example of the present disclosure;

FIGS. 14a-14g schematically illustrate a biopsy tool according to examples of the present disclosure;

DETAILED DESCRIPTION

Figure 11B:
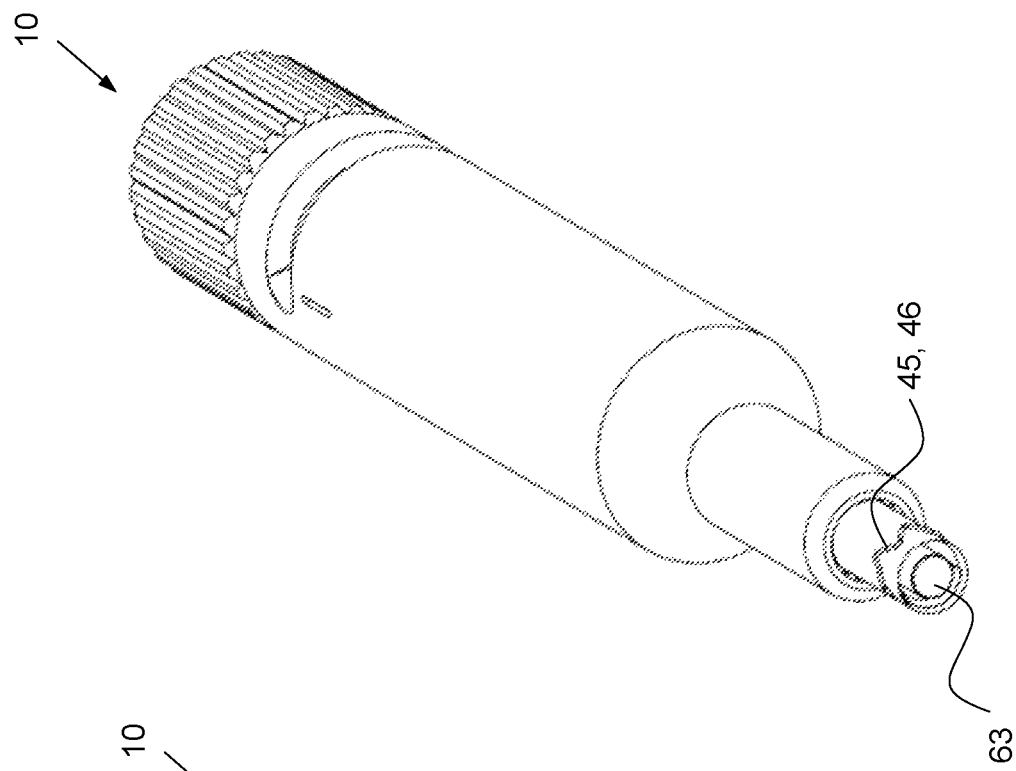
FIGS. 11a-11b schematically illustrate a biopsy tool according to examples of the present disclosure.

The biopsy tool for removing a tissue sample will be described in further detail below. It is understood that all the various examples of the biopsy tool also applies for the method for removing a tissue sample by using such a biopsy tool.

According to an aspect of the present disclosure, a biopsy tool for removing a tissue sample is provided. The biopsy tool is configured to be altered between an incision state and a severing state, the biopsy tool comprising: an elongated outer tubular member extending longitudinally between a proximal end and a distal end, wherein the outer tubular member comprises a first circumferential wall and wherein the distal end of the outer tubular member comprises a cutting edge; an elongated inner tubular member arranged inside the outer tubular member, wherein the inner tubular member comprises a proximal end, a distal end and a second circumferential wall; and a cutting wire, wherein the outer and inner tubular members are rotatable in relation to each other around a rotational axis; wherein the outer tubular member comprises a first aperture in the first circumferential wall and the inner tubular member comprises a second aperture in the second circumferential wall, wherein the first and second apertures extend in a direction perpendicular to the rotational axis, wherein the cutting wire is spring biased and is configured to be arranged in association with the first aperture of the outer tubular member, wherein the biopsy tool is configured to obtain the severing state by rotational movement of the outer tubular member and/or the inner tubular member, so that the first aperture and the second aperture overlap, whereby the cutting wire is displaced perpendicularly to the rotational axis.

The biopsy tool as disclosed may be used for removing a tissue sample from body. The biopsy tool as disclosed may be used for removing a tissue sample from a patient. The patient may be a living human or animal. However, biopsies may also be used in post-mortem investigations as an opportunity to obtain tissue samples for investigating cause of death, for medical studies etc. Thus, the biopsy tool may also be used for removing a tissue sample from a dead human or animal body. This means that the biopsy tool may be used for removing a tissue sample from living tissue and/or dead tissue.

The biopsy tool is configured to be altered between an incision state and a severing state. Due to the two different states, both incision and severing may be accomplished by means of one and the same tool. This means that there is no need for any additional tool, such as forceps, scissor or scalpels, to remove the tissue sample from the sampling area. In the incision state, a first cut extending into the tissue may be conducted. In the severing state, a second cut in a direction perpendicular to the first cut may be conducted, whereby the tissue sample is cut off from the tissue.

Since the outer tubular member has an elongated tubular shape and a cutting edge arranged at its distal end, the elongated outer tubular member is thus configured as a hollow, cylindrical scalpel. By means of the cutting edge, the biopsy tool may in the incision state be used to cut into a tissue, e.g. into skin tissue. The cutting edge may have an annular cross-section. An annular incision cut may thereby be obtained. The cutting edge may be rotated in order to cut down about 5 millimetres (mm) to the layer of fat tissue below the dermis. Alternatively, the cutting edge may be punched down to the fat tissue. The cutting edge may be continuous along the distal end of the outer tubular member. The cutting edge may be configured as an annular cutting blade. The cutting edge may cut when turned, i.e. rotated or twisted, around the rotational axis. The rotation may be clockwise and/or counter clockwise. Skin thickness is different on different parts of the body and the depth of the incision may thus be adjusted according to the current sampling area and the type of tissue sample to be taken. According to examples, the incision by means of the cutting edge may cut down to a depth of between 3-20 mm, or 4-16 mm, or 5-12 mm. The cutting edge may comprise a sharpened material suitable for making an incision in body tissue. According to an example, the cutting edge and the outer tubular member may consist of the same material. According to an example, the cutting edge may be integrated with the outer tubular member. According to an example, the outer tubular member and the cutting edge may comprise different materials. According to a specific example, the outer tubular member may comprise a transparent material and the cutting edge may comprise metal.

By the expression "elongated tubular member" as used herein means an elongated hollow cylinder. The inner and outer tubular members have an annular cross-section. The annular cross-section of the inner and outer tubular members is in a plane perpendicular to the longitudinal direction of the inner and outer tubular member.

The inner and outer tubular member may comprise corrosion resistant stainless steel, surgical steel, plastic or any other suitable material. According to an example, the outer tubular member and/or the inner tubular member may comprise a transparent material. The transparent material may comprise glass, plastics or any other suitable material having transparent properties. According to an example, the outer tubular member may comprise a transparent material and the cutting edge may comprise a surface of diamond dust. By means of the transparent material, the user may be able to see through the outer and/or inner tubular members. This feature facilitates the positioning of the biopsy tool at the tissue sampling area. Thus, by means of the tranparent properties, the user may be able to visually check that the sampling position is correct before initiating the incision. The user may thus check that a skin lesion, which is intended to be removed, is properly centered within the outer and inner tubular elements prior to initiating the sampling procedure.

The biopsy tool comprises a cutting wire. According to an example, the thickness of the cutting wire may be 0.15 mm. According to other examples, the thickness of the cutting wire may be between 0.05-0.5 mm, or between 0.1-0.4 mm, or between 0.15-0.3 mm. The cutting wire may comprise diamond elements. The cutting wire cutting may for example be impregnated with diamond dust of various sizes for efficient cutting of tissue.

According to the present disclosure, the outer and inner tubular members are rotatable. The inner and outer tubular members are coaxially arranged. The rotational axis is thus the same for the outer tubular member and the inner tubular member. By means of the outer and inner tubular members being rotatable, the position of the first aperture and the second aperture may be adjusted in relation to each other. According to an example, the inner tubular member is rotatable in relation to the outer tubular member. According to another example, the outer tubular element is rotatable in relation to the inner tubular member.

The first aperture may be configured with length extending along the circumference of the outer tubular member and a width extending in parallel with the rotational axis. According to an example, the configuration of the first aperture may be adapted to the thickness of the cutting wire. Thus, the width of the first aperture may be approximately 0.5 mm so that the cutting wire may have sufficient space when arranged in association with the first aperture. According to other examples, the width of the first aperture may be between 0.05-1.5 mm, or 0.1-1 mm, or 0.15-0.7 mm.

When removing a tissue sample by means of the biopsy tool as disclosed herein, an incision into the tissue may be performed by means of the cutting edge of the outer tubular member. When performing the incision, the biopsy tool is arranged in the incision state. The cutting edge may provide a substantially annular incision around the tissue sample when the biopsy tool is in the incision state. The remaining bottom part of the tissue sample, which is still attached to the object being sampled after the incision, may be regarded as the base of the tissue sample. When incision is made by means of the cutting edge in body tissue such as skin, the elasticity of the body tissue may lead to that a gap is formed along the incision, in which the first and second circumferential walls may be introduced when cutting deeper. When the incision has been made to a desired tissue sampling depth, the cutting wire and the first and second apertures are then situated in the tissue, e.g. in the layer of fat tissue below the dermis for a skin sample.

The displacement of the cutting wire is then initiated by rotation of the inner and outer tubular member in relation to each other. The outer tubular member and/or the inner tubular member is then rotated, so that the first aperture and the second aperture overlap, whereby the severing state is obtained. As there is nothing that blocks the spring biased cutting wire in the severing state, the cutting wire may be displaced by spring force. Due to the configuration of the biopsy tool, the movement of the spring biased cutting wire may be guided by the first and second apertures. The cutting wire is displaced perpendicularly to the rotational axis by means of spring force. The cutting wire may thus be displaced radially towards the centre of the outer and inner tubular members. Hence, the spring biased cutting wire makes a cutting movement, i.e. a severing movement, in a direction perpendicular to the rotational axis and thereby cuts off at least a part of the base of the tissue sample from the object being sampled. Thus, the cutting wire is arranged perpendicular to the rotational axis, across the hollow interiors of the elongated inner and outer tubular member, in the severing state. By means of the cutting wire being spring biased, the cutting wire may constantly have a proper tension for making a clean cut.

Next, by rotating the biopsy tool around the rotational axis, a further cutting off movement, i.e. severing movement, may be conducted, so that the entire base of the tissue sample is separated from the object being sampled. Thus, by rotating the biopsy tool when being in the severing state, the cutting wire will be rotated and thereby cut off the tissue sample. Thereby, the removal of the sample tissue may be obtained by means of the biopsy tool, without the assistance of other tools. According to an example, the rotation of the biopsy tool around the rotational axis when being in the severing state, may comprise rotation of the entire biopsy tool or rotation of parts of the biopsy tool. Thus, according to an example, rotation around the rotational axis when being in the severing state may comprise rotation of at least the outer tubular member and the inner tubular member. This means that the outer and inner tubular members may rotate together around the rotational axis in the severing state, whereby the cutting wire may also rotate. Consequently, according to an example, the outer and inner tubular members are configured to rotate together around the rotational axis in the severing state, whereby the cutting wire also rotates. The rotation of at least the outer tubular member and the inner tubular member around the rotational axis may thus be a joint rotation. Thus, according to an example, the rotation around the rotational axis may comprise rotation of the outer tubular member, the inner tubular member and the cutting wire. According to an example, the rotation of the biopsy tool, or rotation of at least the outer tubular member and the inner tubular member, around the rotational axis when being in the severing state may be manually operated and/or motorized. According to an example, the rotation around the rotational axis may thus be actuated by a movable knob, a handwheeel, push button etc.

According to an example, the outer tubular member and the inner tubular member are arranged so that the cutting wire abuts an envelope surface of the second circumferential wall in the incision state. By means of this configuration, the spring biased cutting wire is prevented from being displaced by the envelope surface of the second circumferential wall of the inner tubular member in the incision state. Thereby, the spring biased cutting wire is unable to move into a severing state. In the incision state, the spring biased cutting wire may be arranged along the periphery of the second circumferential wall of the inner tubular member. The hollow interiors of the elongated inner and tubular members is thus in an incision state open and accessible for receiving the tissue sample.

According to an example, the first aperture extends circumferentially along at least half the circumference of the outer tubular member and the second aperture extends circumferentially along at least half the circumference of the inner tubular member. By means of that the first aperture and the second aperture extend circumferentially along at least half the circumference of the outer and the inner tubular member, respectively, the entire base of the tissue sample may be cut off. In the severing state, at least half of the base of the tissue sample may be cut off by means of spring force. By rotating the biopsy tool, or at least the outer tubular member and the inner tubular member, in a severing state, i.e. when the cutting wire is arranged across the hollow interiors of the outer and inner tubular member, the remaining part of the base of the tissue sample may be cut off. Thereby, the removal of the sample tissue may be obtained by means of the biopsy tool, without the assistance of other tools.

According to an example, the first aperture extends circumferentially along approximately half the circumference of the outer tubular member and the second aperture extends circumferentially along approximately half the circumference of the inner tubular member.

Alternatively, the first aperture extends circumferentially along less than half the circumference of the outer tubular member and the second aperture extends circumferentially along less than half the circumference of the inner tubular member. If the first aperture and the second aperture extend circumferentially along less than half the circumference of the outer and the inner tubular member, respectively, the entire base of the tissue sample may not be cut off. Thus, a centre portion of the base of the tissue sample may still be attached to the object being sampled after incision, severing and rotating of at least parts of the biopsy tool. The remaining centre portion may then be pulled or cut off by means of assistance of other tools, such as forceps, scissors and/or scalpels.

The first aperture may be arranged at a certain distance from the distal end of the outer tubular member. According to an example, the first aperture may be arranged approximately 2 mm from the distal end of the outer tubular member. According to other examples, the first aperture may be arranged at 0.1-7 mm, or 1-3 mm, from the distal end of the outer tubular member.

According to an example, the first aperture and/or the second aperture may have an outline of a substantially rectangular slot. According to an example, the first aperture and/or the second aperture may have an outline of a substantially rectangular slot comprising rounded corners. By means of a substantially rectangular shape of the first aperture, the cutting wire may be held in place in the incision state. By means of a substantially rectangular shape of the first aperture and the second aperture, the cutting wire may be effectively guided in the direction perpendicular to the rotational axis in the severing state. According to an example, the second aperture may have an outline of a diamond shaped slot. By means of the second aperture having an outline of a diamond shaped slot, the cutting wire may efficiently be guided. The displacement of the cutting wire may then be directed to end corners of the diamond shaped slot. According to an example, the distal end of the inner tubular member may be semi cylindrical. Thus, the second aperture in the inner tubular member may be semi-circular. The semi-circular distal end of the inner tubular member may thus comprise the envelope surface of the second circumferential wall, preventing the spring biased cutting wire from being displaced in the incision state. A semi-circular aperture may be beneficial since it is easy to manufacture. According to an example, the second aperture extends longitudinally from the distal end of the inner tubular member and beyond the first aperture of the outer tubular member in a proximal direction. This configuration of the second aperture may facilitate manufacturing of the biopsy tool.

According to an example, the inner tubular member may be arranged so that the distal end of the inner tubular member is arranged between the first aperture and the distal end of the outer tubular member. According to an example, the inner tubular member may be arranged so that the distal end of the inner tubular member is arranged between the first aperture and the cutting edge of the outer tubular member. By means of this configuration, the distal end of inner tubular member may thus not obstruct the incision of the tissue by means of the cutting edge arranged at the distal end of the outer tubular member.

According to an example, the distal end of the inner tubular member comprises a cutting edge. According to an example, the cutting edge of the inner tubular member may be continuous along the distal end of the inner tubular member. By means of having a cutting edge on both the inner and outer tubular member, a deeper incision cut may be obtained.

According to an example, the cutting wire is displaced perpendicularly to the rotational axis by means of at least one spring element. The biopsy tool may thus comprise at least one spring element. According to an example, the cutting wire is spring biased by means of at least one spring element. The at least one spring element may comprise a helical spring, a telescopic spring, a zig zag spring or any other type of spring or resilient component. Due to the at least one spring element, a semiautomatic severing is achieved in the severing state, when the cutting wire is displaced by means of spring force.

According to an example, the cutting wire comprises two ends, wherein each end is coupled to the at least one spring element. According to an example, the cutting wire may have a thickness of approximately 0.15 mm and the at least one spring element may have a thickness of 0.3 mm. According to another example, the cutting wire may have a thickness of approximately 0.05-0.5 mm and the at least one spring element may have a thickness of 0.1-3 mm. The cutting wire may be thinner than the at least one spring element in order to achieve an efficient and clean cut. The at least one spring element may be thicker than the cutting wire in order to facilitate effective spring characteristics without breaking. However, according to an example, the cutting wire and the at least one spring element may have equal thickness.

According to an example, the at least one spring element is arranged along the periphery of the first circumferential wall of the outer tubular member. According to an example, the cutting wire and the at least one spring element encircle the outer tubular member in an incision state. The at least one spring element and the cutting wire may thus be arranged around at least part of the circumference of the outer tubular member. By means of such a configuration, the cutting wire may be easily installed and/or replaced. Other benefits are that the configuration is simple and the strain on the cutting wire and the at least one spring element are low.

According to an example, the at least one spring element may comprise at least one zig zag spring. A zig zag spring is beneficial since efficient spring characteristics may be obtained while the zig zag spring is almost flat in one extent. The zig zag spring may thus be arranged along the periphery of the outer tubular member and still fit into the gap that arises between the cutting edge and the tissue due to the elasticity of the surrounding tissue when an incision is made. By altering the configuration of the zig zag spring, such as the angle of the folding of each zig zag etc., the characteristics of the spring may be adapted to the current sampling application.

According to an example, the at least one spring element comprises at least one helical spring. By means of helical spring, a reliable and efficient spring characteristics may be obtained for continuously holding the cutting wire properly tensioned.

According to an example, the cutting wire is arranged to extend along the periphery of the outer tubular member through two openings in the first circumferential wall into the outer tubular member. According to an example, the two opening in the first circumferential wall may be configured as slots extending from the distal end of the outer tubular member. The cutting wire may thus extend into the hollow interior of the outer tubular member. In the incision state, the cutting wire will then abut the inside of the first circumferential wall of the outer tubular member and the outside of the second circumferential wall of the inner tubular member. The two openings in the first circumferential wall may be arranged opposite each other. The two openings may be arranged essentially centrally on the first circumferential wall. The two openings may be arranged, so that the cutting wire inside the outer tubular member will follow essentially half the circumference of the first circumferential wall in the incision state. By means of this configuration, the position of the cutting wire may be more fixed.

According to an example, the rotation of the outer and inner tubular members in relation to each other is manually operated and/or motorized. According to an example, the rotation of the biopsy tool, or the rotation of at least the outer tubular member and the inner tubular member, around the rotational axis when being in the severing state may be manually operated and/or motorized. Thus, according to an example, the rotation of at least the outer tubular member and the inner tubular member around the rotational axis may comprise manually operated and/or motorized rotation. Manually operated solutions are simple and cost-effective. Motorized solutions may lead to a biopsy tool which is easier to operate for the user.

According to an example, the biopsy tool comprises a housing. According to an example, the proximal end of the outer tubular member is coupled to the housing.

According to an example, the biopsy tool comprises a gripping portion. The gripping portion may facilitate easy and secure gripping of the biopsy tool by means of one hand. According to an example, the gripping portion may be fixedly arranged to the housing. Thus, the gripping portion may be non-rotatable, i.e. rotatably fixed, in relation to the housing.

According to an example, the biopsy tool comprises an actuator arrangement for rotating the outer and inner tubular members in relation to each other. By means of the actuator arrangement, the biopsy tool may be set in a severing state, an incision state or an intermediate state. The actuator arrangement may comprise a manoeuvring element. The manoeuvring element may comprise a movable knob, a handwheeel, push button etc. The manoeuvring element may actuate a manually operated and/or motorized rotation. The manoeuvring element may be connected to the inner tubular member or the outer tubular member in order to enable the rotation of the outer and inner tubular members in relation to each other. According to an example, the manoeuvring element may be arranged in association with the housing.

According to an example, the actuator arrangement may further comprise a corresponding slot for the manoeuvring element. In one example, the corresponding slot for the manoeuvring element may be arranged in the housing. Thus, rotation of the outer and/or inner tubular member may be provided by displacing the manoeuvring element in/along the corresponding slot. In one example, the slot is configured so that the manoeuvring element is displaced about the rotational axis. According to an example, the rotation may be performed by displacing the manoeuvring element linearly along the rotational axis. By means of a transmission, the linear movement along the rotational axis may then be converted into rotary movement of the outer and inner tubular members in relation to each other.

According to an example, the biopsy tool may further comprises an indicator arrangement for indicating when the biopsy tool is in the incision state, the severing state or in an intermediate state. By means of the indicator arrangement, the current state of the biopsy tool may be clearly indicated. Thus, the risk of incorrect handling of the biopsy tool may thus be reduced. According to an example, the indicator arrangement is comprised in the actuator arrangement.

According to an example, the biopsy tool comprises a measuring arrangement for incision depth. The measuring arrangement may indicate to the user how deep the cutting edge has been inserted into the tissue in the incision state. According to an example, the measuring arrangement may comprise a ruled scale at the outer tubular member. The scale or gradation, in e.g. mm (millimetres), may be visible from the side of the outer tubular member. According to example, the measuring arrangement may comprise a sliding measuring rod. The measuring rod may be slidingly arranged outside the outer tubular member parallel to the rotational axis. One end of the measuring rod may be arranged at the surface of the surrounding tissue of the tissue sample. When incising, the measuring rod may then slide in relation to the outer tubular member. The displacement of the measuring rod may thus correspond to the incision depth. The measuring arrangement may allow reading out a measurement on a ruled scale or a digital display. Thus, by means of the measuring arrangement for incision depth, the current depth of the incision into the tissue may be clearly indicated. By means of the measuring arrangement for incision depth, the risk of severing the tissue sample at an incorrect depth may be reduced.

According to an example, the biopsy tool comprises a sample ejector. By means of the sample ejector, the collected tissue sample may be ejected from the biopsy tool, without the assistance of other tools, such as forceps etc. When removing tissue samples by assistance of forceps etc., there is risk that the tissue sample may be exposed to crush injuries and/or tensile damages. By means of the sample ejector, the risk of these type of damages of the collected tissue sample may be reduced. Consequently, the collected tissue sample may be more representative and of higher quality, when compared to a tissue sample being removed by means of a forceps, which in turn leads to a more adequate analysis of the tissue sample. According to an example, the sample ejector may only be actuated when the biopsy tool is in an incision state. When the sample ejector is actuated in a severing state, there is risk that the cutting wire may break. Also, the cutting wire may cut the tissue sample in two parts, if the sample ejector is actuated in a severing state. However, if the biopsy tool is not intended to be used again, or if it is beneficial to a have a sample divided into two parts, the sample ejector may be configured to be able to be actuated in the severing state.

According to an example, the sample ejector comprises a spring biased plunger arranged inside the inner tubular member. The sample ejector may be configured to normally be in a non-ejecting state. That means that when the sample ejector is not actuated, the sample ejector is in a non-ejecting position.

According to an example, the spring biased plunger may comprise a sample ejector actuator, a plunger, a spring and an ejector tip. The sample ejector actuator may be pushed down in order to eject the collected tissue sample. When the sample ejector is actuated, the ejector tip of the plunger may be pushed towards the tissue sample so that the tissue sample is ejected from the hollow interior of the outer and inner tubular members. Thereby the tissue sample is ejected from the biopsy tool, without the assistance of other tools, such as forceps etc.

According to an example, the biopsy tool is a hand-held tool. A hand-held tool is light weight and easy to handle by a person. However, the present disclosure may be arranged in a sampling apparatus or be a part of a sampling station. According to an example, the present disclosure may be removably engaged with another device, such as a speculum or the like. In this way, the person conducting the tissue sampling may use the speculum to hold a body cavity open, while simultaneously collecting a tissue sample. This may be particularly useful in allowing a medical professional to collect a tissue sample from e.g. the cervix.

According to an example, the biopsy tool may be a disposable device, i.e. a non-reusable device. Thus, the biopsy tool may only be used once, i.e. for one tissue sample. Alternatively, the biopsy tool may be disposable, but allow for multiple samples to be taken from the same object, such as the same patient, before being discarded. According to another example, the biopsy tool may be reusable. The biopsy tool may thus be adapted to be cleaned and sterilized prior to being reused.

According to an example, the biopsy tool may comprise a disposable portion and a reusable portion. The portion of the biopsy tool in contact with the tissue sample may be disposable, while the remaining portion may be reusable. According to an example, the disposal portion may comprise at least the outer tubular member, the inner tubular member and the cutting wire. According to an example, the disposal portion may comprise at least a part of the sample ejector. According to an example, the disposal portion may comprise the ejector tip and/or the plunger. According to an example, the disposable portion may be releasably coupled to the reusable portion. The disposable portion may be releasably coupled to the reusable portion by at least a coupling. The coupling may comprise a press fit connection, a snap fit connection, a threaded coupling, a quick coupling, a bayonet coupling or other types of connections or couplings. A biopsy tool comprising a disposable portion and a reusable portion may be beneficial, since the disposable portion of the biopsy tool in contact with the tissue sample may easily be thrown away after use, and replaced with a new, unused and sterile disposable portion. Thus, the sterility of the parts of the biopsy tool in contact with the tissue sample is upheld without the need of cleaning and sterilizing the whole biopsy tool between samplings. That the remaining portion, i.e. the reusable portion, may be reused is cost-effective and reduces waste.

According to an example, the biopsy tool may comprise a first module unit and a second module unit connected by a coupling arrangement. According to an example, the first module unit may be exchangeable and/or disposable. Thus, the disposable portion previously mentioned may according to an example comprise the first module unit. The second module unit may be exchangeable and/or reusable. Thus, the reusable portion mentioned above may according to an example comprise the second module unit. According to an example, the first and/or the second module unit may comprise a disposable portion. For example, the first module may comprise the outer tubular member, the inner tubular member and the cutting wire. These parts may be in contact with the tissue sample and may thus be disposable, while the rest of the first module unit may be configured to be reused.

By having a first module unit and a second module unit connected by a coupling arrangement, the biopsy tool may be adapted to the present tissue-sampling situation. For example, assembly of an exchangeable and disposable first module unit with a reusable second module unit may be enabled. According to an example, various first module units comprising outer tubular member and corresponding inner tubular member of different diameters may be connected to the same reusable second module unit. Various second module units of different size and performance characteristics may also be available. Thus, a modular system comprising first and second module units of different geometrical dimensions and strength may be achieved, enabling tissue sampling of different sizes. According to an example, the first module unit may comprise the outer tubular member, the inner tubular member and the cutting wire and the second module unit may comprise the actuator arrangement and the manoeuvring element. For such an example, the first module unit may for example be manufactured comprising an outer tubular member with a diameter of e.g. 1, 2, 3, 4, 5, 6, 7, 8, 9, 10, 11, 12, 13, 14, 15, 16, 17, 18, 19 and 20 millimetres. The different sized first module units may all be connected to the same second module unit by means of the coupling arrangement. The biopsy tool may thus be adapted and tailored for the current application by connecting a first module unit of a suitable size for the present tissue-sampling situation to the second module unit. According to a specific example, a first variant of the second module unit may be configured to cooperate with first module units comprising an outer tubular member in the range of 1-5 mm, and a second variant of the second module unit may be configured to cooperate with first module units comprising an outer tubular member in the range of 6-10 mm. According to an example, a third variant of the second module unit may be configured to cooperate with first module units comprising an outer tubular member in the range of 11-20 mm. Thereby, the second module unit may not have to be overly oversized in order to fit all possible sizes of outer tubular members. Thereby, a less bulky and more slender biopsy tool is achieved, suitable for both larger and smaller tissue sampling. Thus, due to the configuration of first and second module units connected by a coupling arrangement, a versatile and flexible biopsy tool may be achieved.

The coupling arrangement may comprise a press fit connection, a snap fit connection, a threaded coupling, a quick coupling, a bayonet coupling, a clamp coupling or other types of connections or couplings. According to an example, the coupling arrangement may comprise a first coupling part configured to be arranged at the first module unit and a corresponding second coupling part configured to be arranged at the second module unit.

As previously mentioned, the biopsy tool may comprises an actuator arrangement for rotating the outer and inner tubular members in relation to each other. According to an example, the actuator arrangement may comprise a manoeuvring element and a transmission arrangement, whereby linear movement of the manoeuvring element along the rotational axis is converted into rotary movement of the outer and inner tubular members in relation to each other. According to an example, the actuator arrangement may comprise a spring biased manoeuvring element. Thus, the actuator arrangement may comprise a spring member forcing the manoeuvring element to a neutral position. The neutral position may correspond to either the incision state or the severing state. According to an example, the transmission arrangement may comprise ball bearings.

According to an example, the transmission arrangement may comprise at least one guiding pin and at least one corresponding guiding groove. When the manoeuvring element is pushed down along the rotational axis, the linear movement of the manoeuvring element may then be converted into rotary movement by means of the at least one guiding pin sliding in the at least one guiding groove. According to an example, the at least one guiding groove may be arranged in a transmission cylinder element configured to rotate around the rotational axis. According to an example, transmission cylinder element may rotate half a revolution by each actuation of the manoeuvring element. The at least one guiding pins may be are fixed in relation to the manoeuvring element while moving axially in relation to the housing. However, according to another example, the at least one guiding groove may be arranged in the housing.

According to an example, the transmission arrangement may comprise at least one spring biased guiding pin and at least one radially inclined guiding groove. According to the example, the transmission cylinder element may turn 180 degrees around the rotational axis when the manoeuvring element is pushed down. When the axial movement downwards in the guiding groove is completed, the manoeuvring element may go back to a neutral position, i.e. not pushed down, by means of the spring member. The radial inclination of the guiding groove in combination with the spring biased guiding pins may thus assist the spring member in the upward movement when the manoeuvring element goes back to the neutral position.

According to another example, the transmission cylinder element may turn approximately 170 degrees around the rotational axis when the manoeuvring element is pushed down. When the movement downward in the guiding groove is completed, the spring member may force the manoeuvring element to go back to the neutral position and thus the final rotational movement to a full half a revolution, i.e. 180 degrees, may be completed during an upward movement.

The transmission of linear movement to rotational movement may thus rotate the inner tubular member and/or the outer tubular member half a revolution around the rotational axis and consequently displace the cutting wire, i.e. altering the state of the biopsy tool between the incision state and the severing state. According to an example, the transmission cylinder element may be coupled to the inner and/or outer tubular member via at least one intermediate member, transferring the rotational movement. According to an example, the at least one intermediate member may comprise an inner tubular member socket connected to the inner tubular member.

According to an example, the housing may be configured to be dividable along the rotational axis. A dividable solution may be beneficial for manufacturing and assembly of the biopsy tool. According to an example, the first module unit may comprise a two-piece cover configured to be dividable along the rotational axis. By means of having a dividable two piece-cover, assembly of the biopsy tool may be facilitated. Especially the mounting of the cutting wire may be easier when the cover is dividable along the rotational axis, since the access to the inner parts of the biopsy tool may be increased. According to an example, the outer tubular member may be fastened to one of the two pieces of cover, by e.g. moulding or gluing. According to an example, the cutting wire may be coupled to the at least one spring element via a cutting wire socket. The two ends of the cutting wire may be connected to the cutting wire socket by means of a fastening device, wherein the cutting wire socket may be connected to the at least one spring element. The fastening device may comprise a fastening plug, a clamp, screw or any other suitable fastening device holding the two ends of the cutting wire in place. Thus, by means of dividable two-piece cover, a more time- and cost effective assembly of the biopsy tool may be achieved. According to an example, the second module unit may comprise a two-piece cover configured to be dividable along the rotational axis.

According to an example, the outer tubular member comprises a first window aperture in the first circumferential wall, wherein the window aperture extends in a direction perpendicular to the rotational axis. By means of the first window aperture, an operator may be able to visually observe the tissue sample area through the first window aperture. Thereby, the aiming of the biopsy tool may improve, which in turn assures proper tissue sampling. According to the example, the inner tubular member comprises a second window aperture in the second circumferential wall, wherein the second window aperture extends in a direction perpendicular to the rotational axis. The second window aperture may be configured to overlap the first window opening in the incision state. A second window aperture may be needed in configurations where the inner tubular member may block the view through the first window aperture. According to an example, the first window opening may function as an indicator. When the biopsy tool is in the incision state, the first window aperture is unblocked, while in the severing state the first window aperture is blocked by the inner tubular member. This means that by visual observation of the first window aperture, an operator may be able to determine the current state of the biopsy tool. Thus, according to an example, indicator arrangement previously mentioned may comprise the first window aperture. Thus, the first window aperture may indicate when the biopsy tool is in the incision state, the severing state or in an intermediate state.

According to an example of the present disclosure, the biopsy tool may be configured for collecting tissue samples from the skin. However, the present disclosure is also suitable for collecting tissue samples from e.g. the cervix.

According to an aspect of the present disclosure, a method for removing a tissue sample by using a biopsy tool is provided. The biopsy tool is configured to be altered between an incision state and a severing state, the biopsy tool comprising: an elongated outer tubular member extending longitudinally between a proximal end and a distal end, wherein the outer tubular member comprises a first circumferential wall and the distal end of the outer tubular member comprises a cutting edge; an elongated inner tubular member arranged inside the outer tubular member, wherein the inner tubular member comprises a proximal end, a distal end and a second circumferential wall; and a cutting wire, wherein the outer and inner tubular members are rotatable in relation to each other around a rotational axis; wherein the outer tubular member comprises a first aperture in the first circumferential wall and the inner tubular member comprises a second aperture in the second circumferential wall, wherein the first and second apertures extend in a direction perpendicular to the rotational axis, wherein the cutting wire is spring biased and is configured to be arranged in association with the first aperture of the outer tubular member, the method comprises the steps of: incising the tissue by means of the cutting edge of the outer tubular member; rotating the outer tubular member and/or the inner tubular member, so that the first aperture and the second aperture overlap, whereby the severing state is obtained and the cutting wire is displaced perpendicularly to the rotational axis; and rotating at least the outer tubular member and the inner tubular member around the rotational axis.

The method as disclosed herein may be used for removing a tissue sample from a body. The method as disclosed herein may be used for removing a tissue sample from a patient. The patient may be a living human or animal. However, biopsies may also be used in post-mortem investigations as an opportunity to obtain tissue samples for investigating cause of death, for medical studies etc. Thus, the method may also be used for removing a tissue sample from a dead human or animal body. This means that the method may be used for removing a tissue sample from living tissue and/or dead tissue. According to an example, the method may be referred to as a method for removing a tissue sample from non-living humans or animals by using a biopsy tool as disclosed herein. According to an example, the method may be referred to as a method for removing a tissue sample comprising non-living tissue by using a biopsy tool as disclosed herein. According to an example, the method may be referred to as a method for removing a tissue sample consisting of non-living tissue by using a biopsy tool as disclosed herein.

Due to the method step of incising the tissue by means of the cutting edge of the outer tubular member, an incision into the tissue is obtained. When performing the incising step, the biopsy tool is arranged in the incision state. The biopsy tool may be positioned substantially perpendicular to the tissue sampling area, e.g. the skin. The cutting edge may then be rotated around the rotational axis in order to cut down to e.g. the layer of fat tissue below the dermis. The rotation of the cutting edge may be clockwise and/or counter clockwise. According to an example, the rotation of the cutting edge may be performed manually by rotating the entire biopsy tool. According to another example, the rotation of the cutting edge may be motorized. Alternatively, the cutting edge may be punched down to the fat tissue. When the incising has been made to a desired tissue sampling depth, the cutting wire and the first and second apertures are then situated in the tissue, e.g. in the layer of fat tissue below the dermis for a skin sample. At this point, the base part of the tissue sample may still be attached to the object being sampled.

By means of the method step of rotating the outer tubular member and/or the inner tubular member, so that the first aperture and the second aperture overlap, the severing state is obtained. As there is nothing that blocks the spring biased cutting wire in the severing state, the cutting wire may be displaced by spring force. The cutting wire is thus displaced perpendicularly to the rotational axis by means of spring force and guided by the first and second apertures. The cutting wire may thus be displaced radially towards the centre of the outer and inner tubular members. Hence, the spring biased cutting wire makes a cutting movement, i.e. a severing movement, in a direction perpendicular to the rotational axis and thereby cuts off at least a part of the base of the tissue sample from the object being sampled.

According to the method step of rotating at least the outer tubular member and the inner tubular member I around the rotational axis, a further cutting off movement, i.e. severing movement, may be achieved. The rotation of at least the outer tubular member and the inner tubular member around the rotational axis may thus be a joint rotation. This means that at least the outer tubular member and the inner tubular member may rotate together around the rotational axis. According to an example, the whole biopsy tool may be rotated around the rotational axis. According to an example, the biopsy tool, or at least the outer tubular member and the inner tubular member, may be rotated around the rotational axis at least 180 degrees, i.e. at least half a turn. According to an example, the biopsy tool, or the at least the outer tubular member and the inner tubular member, may be rotated around the rotational axis approximately 180 degrees, i.e. half a turn. Thus, by rotating the biopsy tool, or at least the outer tubular member and the inner tubular member, when being in the severing state, the cutting wire will be rotated and thereby cut off the base of the tissue sample from the object being sampled. The biopsy tool, or the at least the outer tubular member and the inner tubular member, may be rotated in any direction. According to examples, the biopsy tool, or at least the outer tubular member and the inner tubular member, may be rotated around the rotational axis at least 270 degrees, or at least 360 degrees, or at least 540 degrees. By further rotation, it may be assured that the tissue sample is completely cut-off before removing the biopsy tool from the patient. Thereby, the risk of a remaining uncut portion of the base of the tissue sample is reduced, which facilitates a more favourable sampling situation for both the patient and the operator.

By means of the steps of incising, rotating the outer tubular member and/or the inner tubular member so that a severing state is obtained, and rotating of at least parts of the biopsy tool in a severing state, an efficient removal of the tissue sample is achieved, despite the technical challenges relating to collecting tissue samples. Thereby, an advantageous method for tissue sampling by using a biopsy tool is achieved, which enables efficient removal of tissue samples without the assistance of other tools.

According to an example, further comprising the step of: prior to incising, rotating the outer tubular member and/or the inner tubular member so that the cutting wire abuts an envelope surface of the second circumferential wall whereby the incision state is obtained. By means of the method step of rotating the outer tubular member and/or the inner tubular member so that the incision state is obtained, the spring biased cutting wire is prevented from being displaced by the envelope surface of the second circumferential wall of the inner tubular member. Thereby, the spring biased cutting wire is unable to move into a severing state. In the incision state, the spring biased cutting wire may be arranged along the periphery of the second circumferential wall of the inner tubular member. The hollow interiors of the elongated inner and tubular members is thus in an incision state open and accessible for receiving and collecting the tissue sample.

According to an example, the method may further comprise the step of: ejecting the tissue sample. The tissue sample may be ejected by means of a sample ejector. By means of the step of ejecting the tissue sample, the collected tissue sample may be ejected from the biopsy tool, without the assistance of other tools, such as forceps etc. When removing tissue samples by assistance of forceps, there is risk of that the tissue sample may be expose the crush injuries and/or tensile damages. By means of method step of ejecting the tissue sample, the risk of these type of damages of the collected tissue sample may be reduced. Consequently, the collected tissue sample may be more representative and of higher quality when compared to a tissue sample that have been removed from a biopsy tool by means of a forceps. Thus, by means of the ejecting step, a more representative tissue sample may be obtained, which in turn leads to a more adequate analysis of the tissue sample.

According to an example, prior to ejecting the tissue sample, the biopsy tool may be removed from the tissue sampling area. The biopsy tool may be relocated so that the tissue sample may be ejected into a petri dish, a sampling container or other storage device.

According to an example, the method may further comprise the step of: prior to ejecting, rotating the outer tubular member and/or the inner tubular member so that the cutting wire abuts an envelope surface of the second circumferential wall whereby the incision state is obtained. This means that the ejecting of the tissue may be actuated when the biopsy tool is in an incision state.

If the collected tissue sample is ejected when the biopsy tool is in a severing state, there is risk that the cutting wire may break. Also, the cutting wire may cut the tissue sample in two parts, if the tissue sample is ejected when the biopsy tool is in the severing state. However, if the biopsy tool is not intended to be used again, or if it is beneficial to a have a tissue sample divided into two parts, the step of ejecting the tissue sample may be performed when the biopsy tool is in the severing state.

According to an example, the step of ejecting the tissue sample may only be initiated when the biopsy tool is in an incision state.

According to an example, the rotating of the outer tubular member and/or the inner tubular member in any of the method steps may be manually operated and/or motorized. According to an example, the rotating of at least the outer tubular member and the inner tubular member around the rotational axis in the method step may be manually operated and/or motorized.

The present disclosure will now be further illustrated with reference to the appended figures, wherein for the sake of clarity and understanding of the disclosure some details of no importance are deleted from the figures. Moreover, the figures shall not be considered drawn to scale as some features may be exaggerated in order to more clearly illustrate the invention.

FIGS. 1a-1c, 4a-4c, 5a-5b, 8a-8d, 9a-9b, 10a-10d, 11a-11b, 12a-12d, 13a-13b, 13d-13e, 15a-15c and 16a-16d schematically illustrates examples of a biopsy tool 10 according to examples of the present disclosure. FIGS. 2a-2b, 3a-3b, 6a-6b, 7a-7b, 13c, 13f, 14a-14g and 16e and 17a-17d schematically illustrates details of a biopsy tool 10 according to examples of the present disclosure.

The biopsy tool 10 as shown in the above mentioned figures is configured to be altered between an incision state (indicated as IS in the figures) and a severing state (indicated as SS in the figures).

FIGS. 1a-1c schematically illustrates four side views of a biopsy tool 10 for removing a tissue sample according to an example of the present disclosure. The four different side views corresponding to a front view, a back view and two side views. FIGS. 4a-4c schematically illustrates perspective views of the example as illustrated in FIGS. 1a-1d. FIG. 5a schematically illustrates a side view of the example as illustrated in FIGS. 1a-1d and 4a-4d, and FIG. 5b shows a cross sectional view A-A of the example shown in FIG. 5a. FIG. 11b shows a perspective view of the example as shown in FIGS. 5a-5b.

Figure 11A:
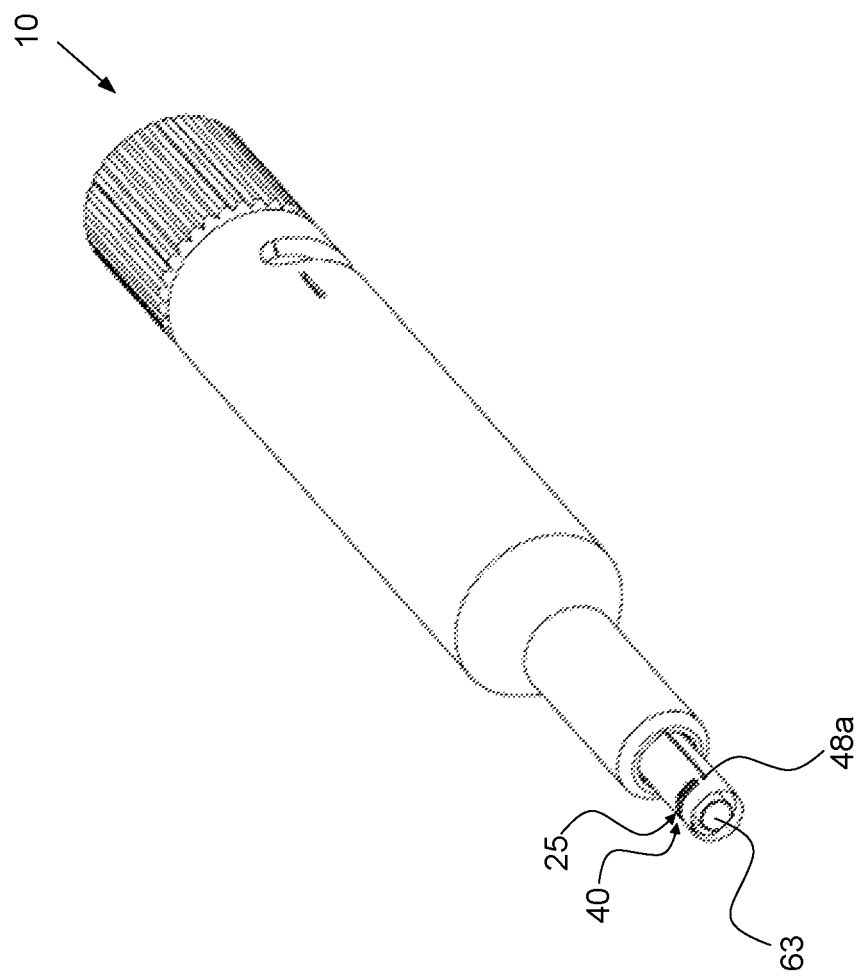

FIGS. 8a-8d schematically illustrates four side views of a biopsy tool 10 for removing a tissue sample according to another example of the present disclosure. The four different side views corresponding to a front view, a back view and two side views. FIGS. 9a-9b schematically illustrates perspective views of the example as illustrated in FIGS. 8a-8d. FIG. 10a-10c schematically illustrates side views of the example as illustrated in FIGS. 8a-8d and 9a-9b. FIG. 10b shows a cross sectional view B-B of the example shown in FIG. 10a. FIG. 10d shows a cross sectional view C-C of the example shown in FIG. 10c. FIG. 11a shows a perspective view of the example as shown in FIGS. 10a-10d.

Figure 15A:
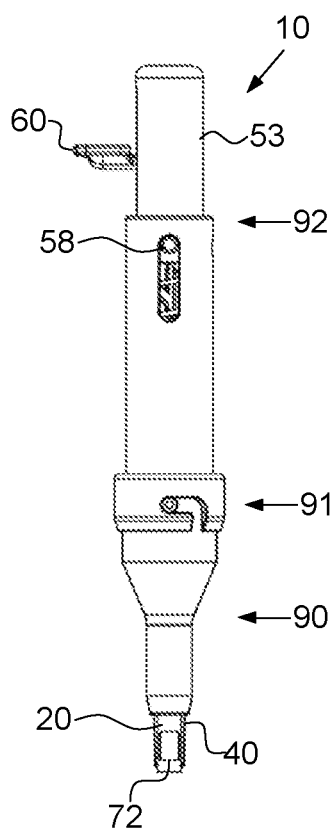
FIGS. 15a-15c schematically illustrate a biopsy tool according to an example of the present disclosure.
Figure 15B:
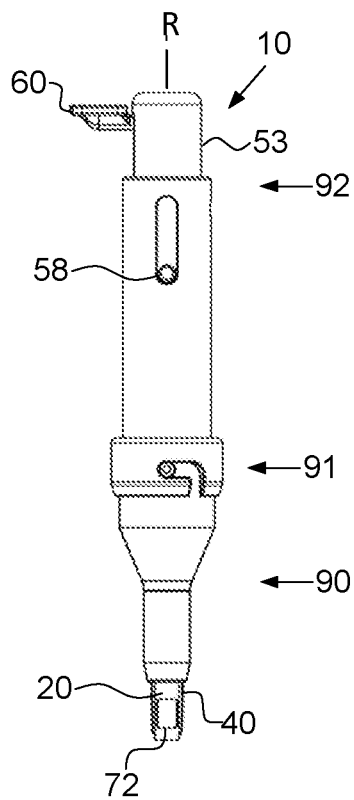
Figure 15C:
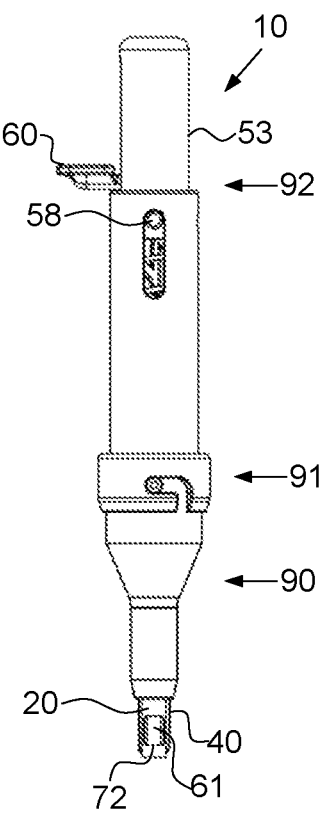
Figure 16A:
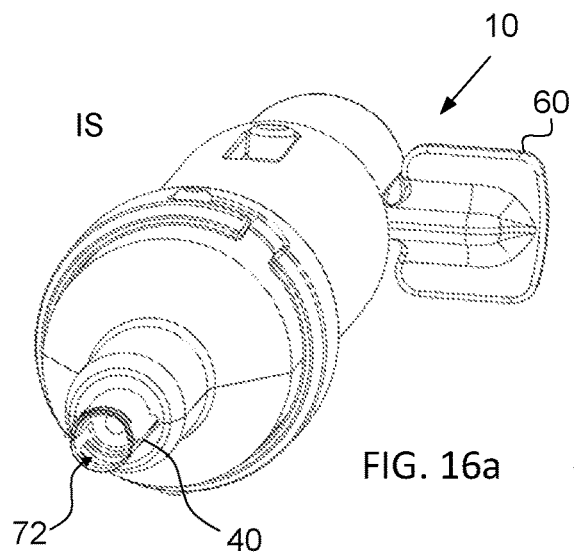
FIGS. 16a-16e schematically illustrate a biopsy tool according to an example of the present disclosure.
Figure 16B:
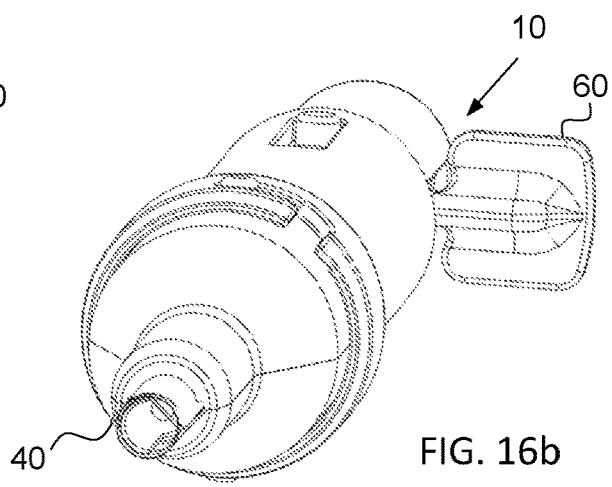
Figure 16C:
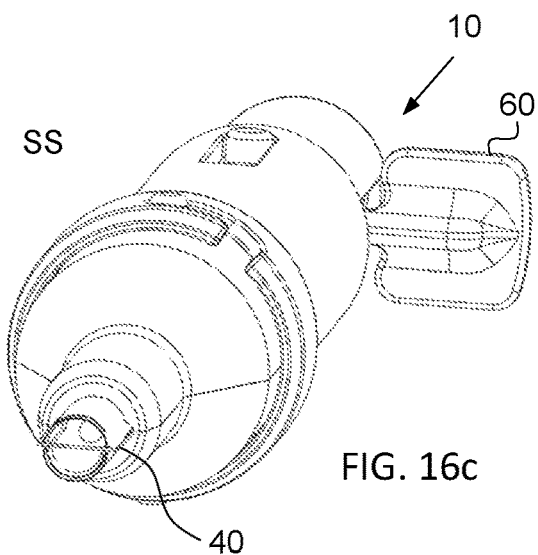
Figure 16D:
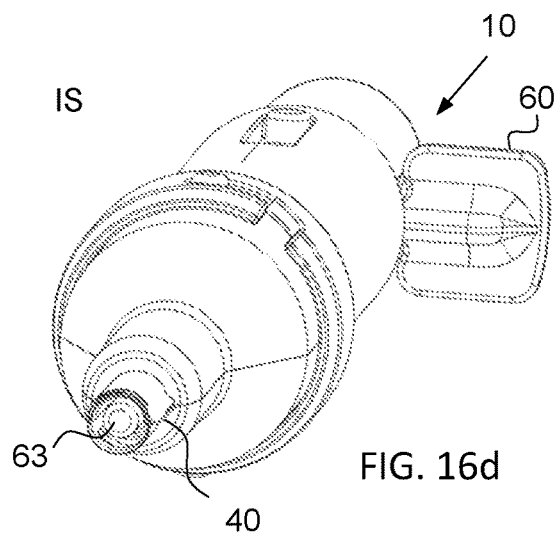
Figure 16E:
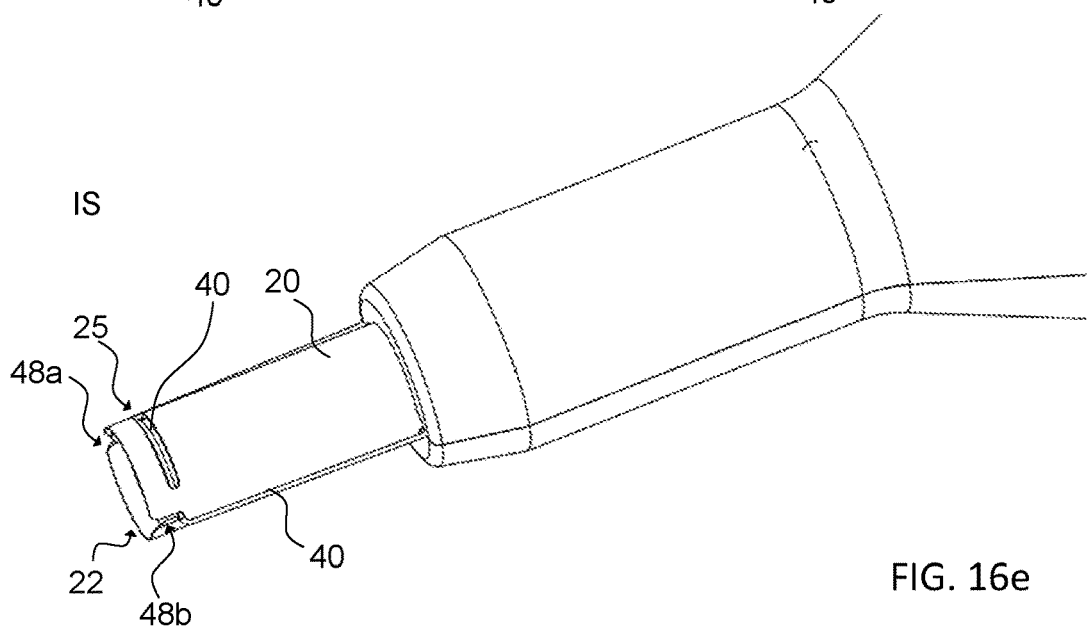

FIGS. 12a-12d schematically illustrate a side view (FIG. 12a) and three perspective views (FIGS. 12b-12c) of a biopsy tool 10 for removing a tissue sample according to another example of the present disclosure. FIGS. 13a-13h schematically illustrate side views of the example as illustrated in FIGS. 12a-12d. FIG. 13b shows a cross sectional view D-D of the example shown in FIG. 13a. FIG. 13c shows a side view of a detail G of the example in FIG. 13a. FIG. 13d shows a side view of a detail H of the example in FIG. 13b. FIG. 13f shows a cross sectional view E-E of the example shown in FIG. 13e. FIG. 13g shows a side view of a detail K of the example in FIG. 13e. FIG. 13h shows a side view of a detail L of the example in FIG. 13f. FIG. 14a-14g schematically illustrates side views and a top view (FIG. 14g) of details of the example as illustrated in FIGS. 12a-12d and 13a-13g. FIG. 14b shows a cross sectional view E-E of the example shown in FIG. 14a. FIG. 14d shows a cross sectional view F-F of the example shown in FIG. 14c. FIGS. 15a-15c schematically illustrate side views of the example as illustrated in FIGS. 12a-12d, 13a-13g and 14a-14b. FIGS. 16a-16d schematically illustrate perespective views of the example as illustrated in FIGS. 12a-12d, 13a-13g, 14a-14d and 15a-15c. FIG. 16c shows a perspective view of details of the example as shown in FIGS. 12a-12d, 13a-13g, 14a-b, 14e-14g, 15a-15c and 16a-16d. FIGS. 17a-17d show side views of details of the present disclosure.

As illustrated in FIGS. 1a-1c, 4a-4c, 5a-5b and 8a-8b, 9a-9b, 10a-10d and 12a-12d, 13a-13h and 16a-16e, the biopsy tool 10 comprises: an elongated outer tubular member 20 extending longitudinally between a proximal end 21 and a distal end 22. The outer tubular member 20 comprises a first circumferential wall 23 and the distal end 22 of the outer tubular member 20 comprises a cutting edge 24. The biopsy tool 10 further comprises an elongated inner tubular member 30 is arranged inside the outer tubular member 20. The inner tubular member 30 comprises a proximal end 31, a distal end 32 and a second circumferential wall 33. The biopsy tool 10 further comprise a cutting wire 40. The outer and inner tubular members 20, 30 are rotatable in relation to each other around a rotational axis R. The outer tubular member 20 comprises a first aperture 25 in the first circumferential wall 23 and the inner tubular member 30 comprises a second aperture 35 in the second circumferential wall 33.

The first and second apertures 25, 35 extend in a direction perpendicular to the rotational axis R. The cutting wire 40 is spring biased and is configured to be arranged in association with the first aperture 25 of the outer tubular member 20. The biopsy tool 10 is configured to obtain the severing state (SS), by rotational movement of the outer tubular member 20 and/or the inner tubular member 30, so that the first aperture 25 and the second aperture 35 overlap, whereby the cutting wire 40 is displaced perpendicularly to the rotational axis R.

FIGS. 2a-2b, 3a-3b, 6a-6b and 7a-7b schematically illustrates details of the outer tubular member 20 and the inner tubular member 30 according to any of the examples as shown in FIGS. 1a-1c, 4a-4c, 5a-5b and 8a-8b, 9a-9b and 10a-10d, 12a-12d, 13a-13h and 16a-16e. In FIGS. 2a-2b, 3a-3b, 6a-6b and 7a-7b, the incision state and severing state is shown in detail. In FIGS. 2b, 3b, 6b and 7b, a severing state is shown, where the first aperture 25 and the second aperture 35 overlap. The cutting wire 40 may then be displaced perpendicularly to the rotational axis R by means of spring force.

When removing a tissue sample by means of the biopsy tool 10, an incision into the tissue may be provided by means of the cutting edge 40 of the outer tubular member 20. When performing the incision, the biopsy tool 10 is arranged in the incision state (IS). The cutting edge 40 may provide a substantially annular incision around the tissue sample when the biopsy tool 10 is in the incision state (IS). The base part of the tissue sample may still be attached to the object being sampled after the incision. When the incision has been made to a desired tissue sampling depth, the cutting wire 40 and the first and second apertures 25, 35 are then situated in the tissue.

After the incision, the outer tubular member 20 and/or the inner tubular member 30 is rotated, so that the first aperture 35 and the second aperture overlap 25, whereby the severing state (SS) is obtained. As there is nothing that blocks the spring biased cutting wire 40 in the severing state (SS), the cutting wire 40 may be displaced due to spring force. Due to configuration of the biopsy tool 10, the movement of the spring biased cutting wire 40 may be guided by the first and second apertures 25, 35. The cutting wire is displaced perpendicularly to the rotational axis R by spring force. The cutting wire may thus be displaced radially towards the centre of the outer and inner tubular members 20, 30. Hence, the spring biased cutting wire 40 makes a cutting movement, i.e. a severing movement, in a direction perpendicular to the rotational axis R. Thereby, at least a part of the base of the tissue sample from the object being sampled may be cut off. Thus, the cutting wire 40 is arranged perpendicular to the rotational axis R, across the hollow interiors of the elongated outer and inner tubular members 20, 30, in a severing state (SS).

Next, by rotating the biopsy tool 10 around the rotational axis R, a further cutting off movement, i.e. severing movement, may be conducted, so the entire base of the tissue sample, is separated from the object being sample. Thus, by rotating the biopsy tool 10 when being in the severing state (SS), the cutting wire 40 will be rotated and thereby cut off the tissue sample. Thereby, the removal of the sample tissue may be obtained by means of the biopsy tool 10, without the assistance of other tools. According to an example, the rotation of the biopsy tool 10 around the rotational axis R when being in the severing state, may comprise rotation of the biopsy tool 10 or rotation of parts of the biopsy tool 10. Thus, according to an example, rotation around the rotational axis R when being in the severing state may comprise rotation of at least the outer tubular member 20 and the inner tubular member 30. This means that the outer and inner tubular members 20, 30 may rotate together around the rotational axis R in the severing state, whereby the cutting wire 40 may also rotate. Thus, the outer and inner tubular members 20, 30 may be configured to rotatate together around the rotational axis R in the severering state, whereby the cutting wire 40 also rotates. According to an example, the rotation of the biopsy tool 10, or rotation of at least the outer tubular member 20 and the inner tubular member 30, around the rotational axis R when being in the severing state may be manually operated and/or motorized.

According to an example, the outer tubular member 20 and the inner tubular member 30 are arranged so that the cutting wire 40 abuts an envelope surface 36 of the second circumferential wall 33 in the incision state (IS). In FIGS. 2a, 3a, 6a and 7a, the incision state is shown in detail. In the incision state (IS), the spring biased cutting wire 40 may be arranged along the periphery of the second circumferential wall 33 of the inner tubular member 30. The hollow interiors of the elongated inner and tubular members 20, 30 is thus in an incision state (IS) open and accessible for receiving the tissue sample.

According to an example, the first aperture 25 may extends circumferentially along at least half the circumference of the outer tubular member 20 and the second aperture 35 extends circumferentially along at least half the circumference of the inner tubular member 30. According to an example, the first aperture 25 extends circumferentially along approximately half the circumference of the outer tubular member 20 and the second aperture 35 extends circumferentially along approximately half the circumference of the inner tubular member 30. Alternatively, the first aperture 25 may extend circumferentially along less than half the circumference of the outer tubular member 20 and the second aperture 35 extends circumferentially along less than half the circumference of the inner tubular member 30.

The first aperture 25 may be arranged in the proximity of the distal end 22 of the outer tubular member 20. The first aperture 25 may be arranged in the proximity of the cutting edge 40 of the outer tubular member 20.

According to an example, the first aperture 25 and/or the second aperture 35 may have an outline of a substantially rectangular slot as illustrated in FIGS. 2a-2b and FIGS. 7a-7b. According to an example, the first aperture 25 and/or the second aperture 35 may have an outline of a substantially rectangular slot comprising rounded corners as illustrated in FIGS. 2a-2b and 3a-3b, 13d, 13h, 16e and 17a-17d. According to an example, the second aperture 35 may have an outline of a diamond shaped slot, as illustrated in FIGS. 6a-6b and 7a-7b. According to an example, the distal end 32 of the inner tubular member 30 may be semi cylindrical as illustrated in FIGS. 3a-3b, 4a-4c, 9a-9b, 13a-13h and 17a-17b. Thus, the second aperture 35 in the inner tubular member 30 may be semi-circular, as illustrated in FIGS. 3a-3b and 17a-17b. According to an example, the second aperture 35 extends longitudinally from the distal end 32 of the inner tubular member 30 and beyond the first aperture 25 of the outer tubular member 20 in a proximal direction as illustrated in FIGS. 3a-3b and 13a-13h and 17a-17b.

According to an example, the inner tubular member 30 may be arranged so that the distal end 32 of the inner tubular member 30 is arranged between the first aperture 25 and the distal end 22 of the outer tubular member 20, as illustrated in e.g. FIGS. 2a-2b, 3a-3b, 4a-4c, 6a-6b, 7a-7b and 9a-9b. According to an example, the inner tubular member 30 may be arranged so that the distal end 32 of the inner tubular member 30 is arranged between the first aperture 25 and the cutting edge 40 of the outer tubular member 20.

According to an example, the distal end 32 of the inner tubular member 30 may comprise a cutting edge 34. According to an example, the cutting wire 40 is displaced perpendicularly to the rotational axis R by means of at least one spring element 45. According to an example, the cutting wire 40 is spring biased by means of at least one spring element 45. According to an example, the cutting wire 40 comprises two ends 41a, 41b, wherein each end 41a, 41b is coupled to the at least one spring element 45, as illustrated in FIGS. 1a, 1d and 10b. In the example shown in FIGS. 13b and 13f, it is also shown that the the cutting wire 40 comprises two ends 41a, 41b, wherein each end 41a, 41b is coupled to the at least one spring element 45.

According to an example, the at least one spring element 45 is arranged along the periphery of the first circumferential wall 23 of the outer tubular member 20, as illustrated in FIGS. 1b-1c and 4a-4c. According to an example, the cutting wire 40 and the at least one spring element 45 encircle the outer tubular member 20 in an incision state (IS), see e.g., FIGS. 1a-1d. The at least one spring element 45 and the cutting wire 40 may thus be arranged around at least part of the circumference of the outer tubular member 20. According to an example, the at least one spring element 45 comprises at least one zig zag spring 46, as illustrated in FIGS. 1a-1d and 4a-4c.

According to an example, the at least one spring element 45 comprises at least one helical spring 47, as illustrated in FIGS. 10a-10c. In FIG. 10a-10b, the biopsy tool 10 is in a incision state, and the helical spring 47 is compressed. In FIG. 10c-10d, the biopsy tool is in a severing state, and the helical spring 47 thus expanded. In the example shown in FIGS. 13a-13f, it is also shown that the at least one spring element 45 comprises at least one helical spring 47. In FIG. 13a-13d, the biopsy tool 10 is in an incision state (IS). In FIGS. 13e-13f, the biopsy tool 10 is in the severing state (SS).

According to an example, the cutting wire 40 is arranged to extend along the periphery of the outer tubular member 20 through two openings 48a, 48b in the first circumferential wall 23 into the outer tubular member 20, as illustrated in FIGS. 8a-8d and 9a-9b. The cutting wire 40 may thus extend into the hollow interior of the outer tubular member 20. In the incision state (IS), the cutting wire 40 will then abut the inside of the first circumferential wall 23 of the outer tubular member 20 and the outside of the second circumferential wall 33 of the inner tubular member 30. The two openings 48a, 48b in the first circumferential wall 23 may be arranged opposite each other. The two openings 48a, 48b may be arranged essentially centrally on the first circumferential wall 23. The two openings 48a, 48b may be arranged, so that the cutting wire 40 inside the outer tubular member 20 will follow essentially half the circumference of the first circumferential wall 23 in the incision state (IS). In the example shown in FIGS. 13a-13h and 16a-16h, it is also illustrated that the cutting wire 40 may be arranged to extend along the periphery of the outer tubular member 20 through two openings 48a, 48b in the first circumferential wall 23 into the outer tubular member 20. In FIG. 13a-13h, the two opening 48a, 48b in the first circumferential wall 23 are configured as slots extending from the distal end 22. This is also shown in closer detail in FIG. 16e, where the biopsy tool 10 is shown in the incision state (IS).

According to an example, the rotation of the outer and inner tubular members 20, 30 in relation to each other is manually operated and/or motorized. According to an example, the rotation of the biopsy tool 10 around the rotational axis R when being in the severing state may be manually operated and/or motorized. Thus, according to an example, the rotation of the biopsy tool 10 around the rotational axis R may comprise manually operated and/or motorized rotation of the outer tubular member 20, the inner tubular member 30 and the cutting wire 40.

As illustrated in e.g. FIGS. 1*a*-1*c*, 4*a*-4*c*, 5*a*-5*b*, 8*a*-8*d*, 10*a*-10*d*, the biopsy tool 10 may comprise an actuator arrangement 52 for rotating the outer and inner tubular members 20, 30 in relation to each other. By means of the actuator arrangement 52, the biopsy tool 10 may be set in a severing state (IS), an incision state (SS) or an intermediate state as illustrated in FIGS. 4*a*-4*c*. In FIG. 9*a*-9*b*, the biopsy tool 10 is shown in the incision state (IS) and the severing state (SS). In the example shown in FIGS. 13*b*, 13*f* and 14*a*-14*d*, it is also shown that the biopsy tool 10 may comprise an actuator arrangement 52 for rotating the outer and inner tubular members 20, 30 in relation to each other.

According to an example, the biopsy tool comprises a housing 50. According to an example, the proximal end 21 of the outer tubular member 20 is coupled to the housing 50. According to an example, the biopsy tool comprises a gripping portion 56. The gripping portion 56 may facilitate easy and secure gripping of the biopsy tool 10 by means of one hand. According to an example, the gripping portion 56 may be fixedly arranged to the housing 50. Thus, the gripping portion 56 may be non-rotatable, i.e. rotatably fixed, in relation to the housing 50.

The actuator arrangement 52 may comprise a manoeuvring element 53. The manoeuvring element 53 may comprise a movable knob, a handwheeel, push button etc. The manoeuvring element 53 may actuate a manually operated and/or motorized rotation. The manoeuvring element 53 may be coupled to the inner tubular member 30 or the outer tubular member 20 in order to enable the rotation of the outer and inner tubular members 20, 30 in relation to each other. In the examples shown in FIGS. 5*a*-5*b*, 10*a*-10*d* and FIG. 13*a*-13*h*, the actuator arrangement 52 may rotate the inner tubular member 30 in relation to the outer tubular member 20. According to an example, the manoeuvring element 53 may be arranged in association with a housing 50.

According to an example, the actuator arrangement 52 may further comprise a a corresponding slot 55 for the manoeuvring element 53, as shown in e.g. FIGS. 4*a*-4*c* and 9*a*-9*b*. The corresponding slot 55 for the manoeuvring element may be arranged in the housing 50. Thus, rotation of the outer and/or inner tubular member 20,30 may be provided by displacing the manoeuvring element 53 in/along the corresponding slot 55. The slot may be configured so that the manoeuvring element 53 is displaced about the rotational axis R. According to an example, the rotation may be performed by displacing the manoeuvring element 53 linearly along the rotational axis R (not shown in the FIGS. 4*a*-4*c* and 9*a*-9*b*). By means of a transmission, the linear movement along the rotational axis R may then be converted into rotary movement of the outer and inner tubular members 20, 30 in relation to each other.

As illustrated in e.g. FIGS. 1*a*-1*c*, 4*a*-4*c*, 5*a*-5*b*, 8*a*-8*d*, 10*a*-10*d*, the biopsy tool 10 may further comprises an indicator arrangement 54 for indicating when the biopsy tool 10 is in the incision state (IS), the severing state (SS) or in an intermediate state. According to an example, the indicator arrangement 54 is comprised in the actuator arrangement 52. The manoeuvring element 53 may be arranged at the mark "0" which indicates that the biopsy tool is in the incision state (IS), as illustrated in the FIGS. 4*a* and 9*a*. In the severing state (SS), the manoeuvring element 53 may be arranged at the mark "I" as illustrated in FIGS. 4*c* and 9*b*. In FIG. 4*b*, the biopsy tool 10 is in an intermediate state, between the incision state (IS) and the severing state (SS).

As illustrated in FIGS. 5*b*, 10*b*, 10*d* and 11*a*-11*b*, 13*b*, 16*d*, the biopsy tool 10 may comprises a sample ejector 60, 61, 62, 63. According to an example, the sample ejector 60, 61, 62, 63 may comprises a spring biased plunger 61 arranged inside the inner tubular member 30. According to an example, the spring biased plunger 61 may comprise a sample ejector actuator 60, a spring 62 and an ejector tip 63. The sample ejector actuator 60 may be pushed down in order to eject the tissue sample. When the sample ejector 60, 61, 62, 63 is actuated, the ejector tip 63 of the plunger 61 may be pushed towards the tissue sample so that the tissue sample is ejected from the hollow interior of the outer and inner tubular members 20, 30. Thereby the tissue sample is ejected from the biopsy tool 10, without the assistance of other tools, such as forceps etc.

According to an example, the biopsy tool 10 is a hand-held tool as illustrated in FIGS. 1*a*-1*c*, 4*a*-4*c*, 5*a*-5*b*, 8*a*-8*d*, 10*a*-10*d*, 12*a*-12*d*, 13*a*-13*h* and 15*a*-15*c*. However, the biopsy tool 10 may be arranged in a sampling apparatus or be a part of a sampling station. According to an example, the biopsy tool 10 may be removably engaged with another device, such as a speculum or the like.

According to an example, the biopsy tool 10 may comprise a disposable portion 80 and a reusable portion 82, as illustrated in FIGS. 5*b* and 10*b*. The portion of the biopsy tool 10 in contact with the tissue sample may be disposable, while the remaining portion may be reusable. According to an example, the disposal portion 80 may comprise at least the outer tubular member 20, the inner tubular member 30 and the cutting wire 40. According to an example, the disposal portion 80 may comprise at least a part of the sample ejector 60, 61, 62, 63. According to an example, the disposal portion 80 may comprise the ejector tip 63 and/or the plunger 61.

According to the examples schematically illustrated in FIGS. 12*a*-12*d*, 13*a*-13*h*, 14*a*-14*g*, 15*a*-15*c* and 16*a*-16*e*, the biopsy tool 10 may comprise a first module unit 90 and a second module unit 92 connected by a coupling arrangement 91.

According to an example, the first module unit 90 may be exchangeable and/or disposable. Thus, the disposable portion 80 previously mentioned may according to an example comprise the first module unit 90. The second module unit 92 may be exchangeable and/or reusable. Thus, the reusable portion 82 mentioned above may according to an example comprise the second module unit 92. According to an example, the first and/or the second module unit 90, 92 may comprise a disposable portion 80. For example, the first module 90 may comprise the outer tubular member 20, the inner tubular member 30 and the cutting wire 40. These parts may be in contact with the tissue sampling and may thus be disposable, while the rest of the first module unit 90 may be configured to be reused.

By having a first module unit 90 and a second module unit 92 connected by a coupling arrangement 91, the biopsy tool 10 may be adapted to the present tissue-sampling situation. For example, assembly of an exchangeable and disposable first module unit 90 with a reusable second module unit 92 may be facilitated. According to an example, various first module units 90 comprising outer tubular element 20 and corresponding inner tubular element 30 of different diameters may be connected to the same reusable second module unit 92. Various second module units 92 of different size and performance characteristics may also be available. Thus, a modular system comprising first and second module units 90, 92 of different geometrical dimensions and strength may be achieved, enabling tissue sampling of different sizes. According to an example, the first module unit 90 may comprise the outer tubular member 20, the inner tubular member 30 and the cutting wire 40 and the second module unit 92 may comprise the actuator arrangement 52 and the manoeuvring element 53. For such an example, the first module unit 90 may for example be manufactured comprising an outer tubular member 20 with a diameter of e.g. 1, 2, 3, 4, 5, 6, 7, 8, 9, 10, 11, 12, 13, 14, 15, 16, 17, 18, 19, 20 millimetres. The different sized first module units 90 may all be connected to the same second module unit 92 by means of the coupling arrangement 91. The biopsy tool 10 may thus be adapted and tailored for the current application by connecting a first module unit 90 of a suitable size for the present tissue-sampling situation to the second module unit 92. According to a specific example, a first variant of the second module unit 92 may be configured to cooperate with first module units 90 comprising an outer tubular member 20 in the range of 1-5 mm, and a second variant of the second module unit 92 may be configured to cooperate with first module units 90 comprising an outer tubular member 20 in the range of 6-10 mm. According to an example, a third variant of the second module unit 92 may be configured to cooperate with first module units 90 comprising an outer tubular member 20 in the range of 11-20 mm. Thereby, the second module unit 92 may not have to be overly oversized in order to fit all possible sizes of outer tubular members 20. Thereby, a less bulky and more slender biopsy tool is achieved, suitable for both larger and smaller tissue sampling. Thus, due to the configuration of first and second module units 90, 92 connected by a coupling arrangement 91, a versatile and flexible biopsy tool 10 is achieved.

The coupling arrangement 91 may comprise a press fit connection, a snap fit connection, a threaded coupling, a quick coupling, a bayonet coupling, a clamp coupling or other types of connections or couplings. According to an example, the coupling arrangement 91 may comprise a first coupling part 93 configured to be arranged at the first module unit 90 and a corresponding second coupling part 94 configured to be arranged at the second module unit 92. In the example shown in FIGS. 12a-12d, the coupling arrangement 91 comprises a bayonet coupling.

The biopsy tool 10 as shown in the examples in FIGS. 12a-12d, 13a-13h, 14a-14g, 15a-15c and 16a-16e comprises an actuator arrangement 52 for rotating the outer and inner tubular members 20, 30 in relation to each other as previously mentioned. As shown in more detail in FIGS. 14a-14b, the actuator arrangement 52 may comprise a manoeuvring element 53 and a transmission arrangement 57, whereby linear movement of the manoeuvring element 53 along the rotational axis R is converted into rotary movement of the outer and inner tubular members 20, 30 in relation to each other. According to an example, the actuator arrangement 52 may comprises a spring biased manoeuvring element 53. Thus, the actuator arrangement 52 may comprise a spring member 65 forcing the manoeuvring element 53 to a neutral state. The neutral position may correspond to either the incision state or the severing state. According to an example, the transmission arrangement 57 may comprise ball bearings 66.

According to the example shown in detail in FIGS. 14a-14b, the transmission arrangement 57 may comprise at least one guiding pin 58 and at least one corresponding guiding groove 59. When the manoeuvring element 53 is pushed down along the rotational axis R, the linear movement of the manoeuvring element 53 is converted into rotary movement by means of the at least one guiding pin 58 sliding in the at least one guiding groove 59. In the example in FIGS. 14a-14b, the guiding grooves are arranged in a transmission cylinder element 69 configured to rotate around the axis R half a revolution by each actuation of the manoeuvring element 53, the two guiding pins 58 are fixed in relation to the manoeuvring element 53 while moving axially in relation to the housing 50. However, according to another example, the guiding grooves 59 may be arranged in the housing 50.

Another alternative configuration for transmission of linear movement to rotational movement is shown in FIGS. 14c-14d. In this example, the transmission arrangement 57 may comprise at least one spring biased guiding pin 58 and at least one radially inclined guiding groove 59. In FIGS. 14c-14d, the transmission cylinder element 69 turns 180 degrees around the rotational axis R when the manoeuvring element 53 is pushed down. When the axial movement downwards in the guiding groove 59 is completed, the manoeuvring element 53 may go back to a neutral position, i.e. not pushed down, by means of the spring member 65. The radial inclination of the guiding groove 59 in combination with the spring biased guiding pins 58 may thus assist the spring member 65 in the upward movement when the manoeuvring element 53 goes back to the neutral position The guiding groove 59 as shown in FIGS. 14a-14b has a different geometrical configuration, where the transmission cylinder element 69 turns approximately 170 degrees around the rotational axis R when the manoeuvring element 53 is pushed down. When the movement downward in the guiding groove 59 is completed, the spring member 65 forces the manoeuvring element 53 to go back to the neutral position and thus the final rotational movement to a full half a revolution, i.e. 180 degrees, is completed.

The transmission of linear movement to rotational movement as shown in FIGS. 14c-14d thus turns the inner tubular member 30 half a revolution around the rotational axis R and consequently displaced the cutting wire 40, i.e. altering the state of the biopsy tool 10 between the incision state and the severing state. According to an example, the transmission cylinder element 69 may be coupled to the inner and/or outer tubular member 20, 30 via at least one intermediate member, transferring the rotational movement. In the example in FIGS. 13a-13b, the at least one intermediate member may comprise an inner tubular member socket 37 connected to the inner tubular member 30.

In FIG. 15a, the biopsy tool 10 is shown with the manoeuvring element 53 in a neutral position, i.e. not pushed down. This means that the biopsy tool may be in either the incision state or the severing state. A perspective view of the cutting wire 40 in an incision state (IS) is shown in FIG. 16a and in a severing state (SS) in FIG. 16c. In FIG. 15b, the manoeuvring element 53 is pushed fully down, corresponding to when the guiding cylinder 59 has turned approximately 170 degrees, as previously described above. Thus, the biopsy tool 10 is in an intermediate state, between the incision state and the severing state in FIG. 15b. A perspective view of the cutting wire 40 in an intermediate state is shown in FIG. 16b. In FIG. 15c, the biopsy tool may be in the incision state or the severing state.

The sample ejector actuator 60 is pushed down and the spring biased plunger 61 visible through a widow aperture 72 in the outer tubular member 20. A perspective view of the cutting wire 40 in an incision state with the sample ejector actuator 60 pushed down and the ejector tip 63 visible is shown in FIG. 16b.

The actuator arrangement 52 comprising a manoeuvring element 53 and a transmission arrangement 57, whereby linear movement of the manoeuvring element 53 along the rotational axis R is converted into rotary movement have been described with reference to examples of the biopsy tool 10 comprising a first module unit 90 and a second module unit 92 as shown in FIGS. 12a-12d, 13a-13h, 14a-14g, 15a-15c and 16a-16d. However, such manoeuvring element 53 and transmission arrangement 57 may also be applied for the examples shown in FIGS. 1a-1d, 4a-4c, 5a-5b, 8a-8d, 9a-9b, 10a-10d and 11a-11b.

According to an example, the first module unit 90 may comprise a two-piece cover 51 configured to be dividable along the rotational axis R. Such a configuration is schematically disclosed in FIGS. 14e-14g, where one of the two pieces of cover 51 is shown, while the other one of the two pieces of cover is removed. By means of having a dividable two piece-cover 51, assembly of the biopsy tool 10 is facilitated. Especially the mounting of the cutting wire 40 may be easier when the cover is dividable along the rotational axis R, since the access to the inner parts of the biopsy tool 10 may be increased. According to an example, the outer tubular member 30 may be fastened to one of the two pieces of cover 51, by e.g. moulding or gluing. According to an example, the cutting wire 40 may be coupled to the spring element 45 via a cutting wire socket 38. As may be seen in FIGS. 14e-14g, the cutting wire 40 may be easily mounted by laying the cutting wire 40 in the two openings 48a, 48b in the first circumferential wall 23 and fastening the two ends 41a, 41b of the cutting wire 40 to the cutting wire socket 38 by means of a fastening device 39 (seen from above in FIG. 14g), wherein the cutting wire socket 38 is connected to the spring element 45. The fastening device 30 may comprise a fastening plug, a clamp, screw or any other suitable fastening device holding the two ends 41a, 41b of the cutting wire 40 in place. Thus, by means of dividable two-piece cover, a more time- and cost effective assembly of the biopsy tool 10 may be achieved. According to an example, the second module unit 92 may comprise a two-piece cover 51 configured to be dividable along the rotational axis R.

According to another example, the biopsy tool may comprise a housing 50, wherein the housing 50 is configured to be dividable along the rotational axis R. Thus, a dividable casing solution is not only applicable on the first and/or second module unit 90, 92. A dividable solution may also be beneficial for manufacturing and assembly of the biopsy tool 10 according to the examples shown in e.g. FIGS. 5a-5b and 10a-10c.

Figures 17A, 17B:
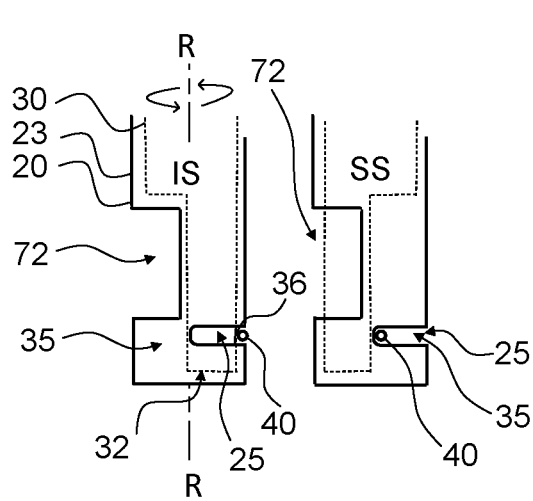
FIGS. 17a-17d schematically illustrate details of a biopsy tool according to examples of the present disclosure.
Figures 17C, 17D:
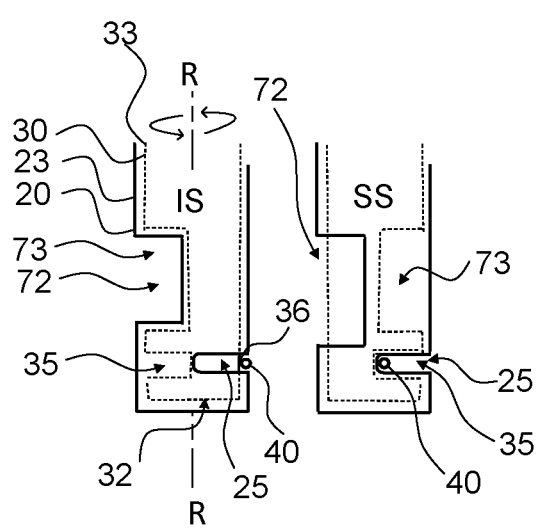

FIGS. 17a-17d schematically illustrates details of the outer tubular member 20 and the inner tubular member 30 according to any of the examples as shown in FIGS. 1a-1c, 4a-4c, 5a-5b and 8a-8b, 9a-9b and 10a-10d, 12a-12d, 13a-13h and 16a-16e. In FIGS. 17a-17c, the incision state and severing state is shown in detail. In FIGS. 17b and 17d, a severing state is shown, where the first aperture 25 and the second aperture 35 overlap. The cutting wire 40 may then be displaced perpendicularly to the rotational axis R by means of spring force. In FIGS. 17a-17d, the outer tubular member 20 comprises a first window aperture 72 in the first circumferential wall 23, wherein the first window aperture 72 extends in a direction perpendicular to the rotational axis R. The first window aperture 72 is also shown in FIGS. 12a-12b, 13a-13h, 14e-14f, 15a-15c and 16a-16b. By means of the first window aperture 72, an operator may be able to visually observe the tissue sample area through the window aperture. Thereby, the aiming of the biopsy tool may improve, which in turn assures proper tissue sampling. According to the example shown in FIG. 17c-17d, the inner tubular member (30) comprises a second window aperture 73 in the second circumferential wall (33), wherein the second window aperture 73 extends in a direction perpendicular to the rotational axis R. The second window aperture 73 may be configured to overlap the first window opening 72 in the incision state. A second window aperture 73 may be needed in configurations where the inner tubular member 30 may block the view through the first window aperture 72. According to an example, the window opening 72 may function as an indicator. When the biopsy tool 10 is in the incision state (IS), the first window aperture 72 is unblocked, while in the severing state (SS) the first window aperture 72 is blocked by the inner tubular member 30. This means that by visual observation of the first window aperture 72, an operator may be able to determine the current state of the biopsy tool 10. Thus, according to an example, indicator arrangement 54 previously mentioned may comprise the first window aperture 72. Thus, the first window aperture 72 may indicate when the biopsy tool 10 is in the incision state, the severing state or in an intermediate state.

Figure 18:
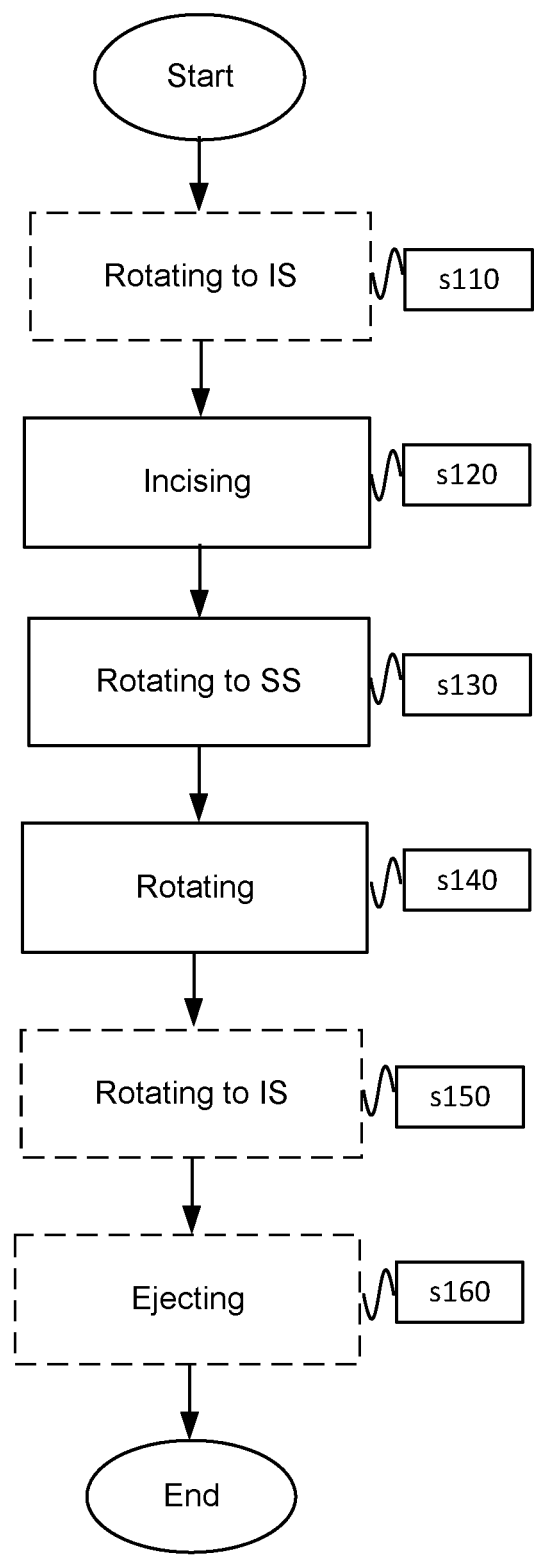
FIG. 18 schematically illustrates a block diagram of method steps according to examples of the present disclosure.

FIG. 18 schematically illustrates a block diagram of a method for removing a tissue sample by using a biopsy tool 10 according to an example. The method relates to the biopsy tool as disclosed in FIGS. 1a-1c, 2a-2b, 3a-3b, 4a-4c, 5a-5b, 6a-6b, 7a-7b, 8a-8d, 9a-9b, 10a-10d, 11a-11b, 12a-12d, 13a-13h, 14a-14d, 15a-15c, 16a-16e and 17a-17d.

The method comprises the steps of: incising s120 the tissue by means of the cutting edge 24 of the outer tubular member 20; rotating s130 the outer tubular member 20 and/or the inner tubular member 30, so that the first aperture 25 and the second aperture 35 overlap, whereby the severing state SS is obtained and the cutting wire 40 is displaced perpendicularly to the rotational axis R; and rotating s140 at least the outer tubular member 20 and the inner tubular member 30 around the rotational axis R.

The method may further comprise the step of: prior to incising s120, rotating s110 the outer tubular member 20 and/or the inner tubular member 30 so that the cutting wire 40 abuts an envelope surface 36 of the second circumferential wall 33 whereby the incision state (IS) is obtained.

The method may further comprise the step of: ejecting s160 the tissue sample.

According to an example, prior to ejecting s160 the tissue sample, the biopsy tool 10 may be removed from the tissue sampling area. The biopsy tool may be moved so that the tissue sample may be ejected into a petri dish, a sampling container or other storage device.

The method may further comprise the step of: prior to ejecting s160, rotating s150 the outer tubular member 20 and/or the inner tubular member 30 so that the cutting wire 40 abuts an envelope surface 36 of the second circumferential wall 33 whereby the incision state (IS) is obtained.

According to an example, the rotating of the outer tubular member 20 and/or the inner tubular member 30 in any of the method steps s110, 130, s150 may be manually operated and/or motorized. According to an example, the rotating of at least the outer tubular member 20 and the inner tubular member 30 in the method step s140 may be manually operated and/or motorized.

The foregoing description of the preferred examples of the present disclosure is provided for illustrative and descriptive purposes. It is not intended to be exhaustive or to restrict the invention to the variants described. Many modifications and variations will obviously be apparent to one skilled in the art. The examples of the present disclosure have been chosen and described in order best to explain the principles of the invention and its practical applications and hence make it possible for specialists to understand the invention for various embodiments and with the various modifications appropriate to the intended use.

The invention claimed is:

1. A biopsy tool for removing a tissue sample, the biopsy tool being configured to be altered between an incision state and a severing state, the biopsy tool comprising:
    an elongated outer tubular member extending longitudinally between a proximal end and a distal end, wherein the outer tubular member includes a first circumferential wall, and wherein the distal end of the outer tubular member includes a cutting edge;
    an elongated inner tubular member arranged inside the outer tubular member, wherein the inner tubular member includes a proximal end, a distal end, and a second circumferential wall; and
    a cutting wire;
    wherein the outer and the inner tubular members are rotatable in relation to each other around a rotational axis;
    wherein the outer tubular member includes a first aperture in the first circumferential wall and the inner tubular member includes a second aperture in the second circumferential wall, wherein the first and the second apertures extend in a direction perpendicular to the rotational axis;
    wherein the cutting wire is spring biased and is arranged in association with the first aperture of the outer tubular member;
    wherein the biopsy tool is configured to obtain the severing state by rotational movement of the outer tubular member and/or the inner tubular member, so that the first aperture and the second aperture overlap, whereby the cutting wire is displaced perpendicularly to the rotational axis by means of spring force;
    wherein the cutting wire is spring biased against a peripheral surface of the inner tubular member during the incision state in which a first cut into the tissue is conducted.

2. The biopsy tool according to claim 1, wherein the outer tubular member and the inner tubular member are arranged so that the cutting wire abuts an envelope surface of the second circumferential wall in the incision state.

3. The biopsy tool according to claim 1, wherein the first aperture extends circumferentially along at least half the circumference of the outer tubular member; and
    wherein the second aperture extends circumferentially along at least half the circumference of the inner tubular member.

4. The biopsy tool according to claim 1, wherein the inner tubular member is arranged so that the distal end of the inner tubular member is arranged between the first aperture and the distal end of the outer tubular member.

5. The biopsy tool according to claim 1, wherein the distal end of the inner tubular member comprises a cutting edge.

6. The biopsy tool according to claim 1, wherein the cutting wire is spring biased by at least one spring element.

7. The biopsy tool according to claim 6, wherein the cutting wire comprises two ends, wherein each end is coupled to the at least one spring element.

8. The biopsy tool according to claim 6, wherein the at least one spring element is arranged along the periphery of the first circumferential wall of the outer tubular element.

9. The biopsy tool according to claim 6, wherein the cutting wire and the at least one spring element encircle the outer tubular member in an incision state.

10. The biopsy tool according to claim 6, wherein the at least one spring element comprises at least one zig zag spring or at least one helical spring.

11. The biopsy tool according to claim 1, wherein the cutting wire is arranged to extend along the periphery of the outer tubular member through two openings in the first circumferential wall into the outer tubular member.

12. The biopsy tool according to claim 1, wherein rotation of the outer and the inner tubular members in relation to each other is manually operated and/or motorized.

13. The biopsy tool according to claim 1, wherein the biopsy tool further comprises an actuator arrangement for rotating the outer and the inner tubular members in relation to each other.

14. The biopsy tool according to claim 13, wherein the actuator arrangement comprises a maneuvering element and a transmission arrangement, whereby linear movement of the maneuvering element along the rotational axis is converted into rotary movement of the outer and the inner tubular members in relation to each other.

15. The biopsy tool according to claim 1, wherein the biopsy tool further comprises an indicator arrangement for indicating when the biopsy tool is in the incision state, the severing state, or in an intermediate state.

16. The biopsy tool according to claim 1, wherein the biopsy tool further comprises a sample ejector.

17. The biopsy tool according to claim 16, wherein the sample ejector comprises a spring biased plunger arranged inside the inner tubular member.

18. The biopsy tool according to claim 1, wherein the biopsy tool is a hand-held tool.

19. The biopsy tool according to claim 1, wherein the biopsy tool comprises a disposable portion and a reusable portion.

20. The biopsy tool according to claim 1, wherein the outer and the inner tubular members are configured to rotate together around the rotational axis in the severing state, whereby the cutting wire also rotates.

21. The biopsy tool according to claim 1, wherein the biopsy tool comprises a first module unit and a second module unit connected by a coupling arrangement.

22. A method for removing a tissue sample by using a biopsy tool, the biopsy tool being configured to be altered between an incision state and a severing state, the biopsy tool including,
    an elongated outer tubular member extending longitudinally between a proximal end and a distal end, wherein the outer tubular member includes a first circumferential wall, and wherein the distal end of the outer tubular member includes a cutting edge,
    an elongated inner tubular member arranged inside the outer tubular member, wherein the inner tubular member includes a proximal end, a distal end, and a second circumferential wall, and
    a cutting wire,
    wherein the outer and the inner tubular members are rotatable in relation to each other around a rotational axis,
    wherein the outer tubular member includes a first aperture in the first circumferential wall and the inner tubular member includes a second aperture in the second circumferential wall, wherein the first and the second apertures extend in a direction perpendicular to the rotational axis, wherein the cutting wire is spring biased and is arranged in association with the first aperture of the outer tubular member, wherein the cutting wire is spring biased against a peripheral surface of the inner tubular member during the incision state in which a first cut into the tissue is conducted, the method comprising:

incising the tissue by means of the cutting edge of the outer tubular member;

rotating the outer tubular member and/or the inner tubular member, so that the first aperture and the second aperture overlap, whereby the severing state is obtained and the cutting wire is displaced perpendicularly to the rotational axis by means of spring force; and rotating at least the outer tubular member and the inner tubular member around the rotational axis.

23. The method according to claim 22, further comprising:
prior to incising, rotating the outer tubular member and/or the inner tubular member so that the cutting wire abuts an envelope surface of the second circumferential wall whereby the incision state is obtained.

24. The method according to any of the claim 22, further comprising:
ejecting the tissue sample.

25. The method according to claim 24, further comprising:
prior to ejecting, rotating the outer tubular member and/or the inner tubular member so that the cutting wire abuts an envelope surface of the second circumferential wall whereby the incision state is obtained.

* * * * *